United States Patent [19]

Tanaka et al.

[11] Patent Number: 4,963,449

[45] Date of Patent: Oct. 16, 1990

[54] P-AMINO SUBSTITUTED TETRAPHENYLTHIOPHENES AND ELECTROPHOTOGRAPHIC PHOTORECEPTORS CONTAINING THEM

[75] Inventors: Eishi Tanaka, Kyoto; Tsutomu Nishizawa, Yokohama; Yasuyuki Yamada, Yokohama, Hisato Itoh, Yokohama; Akihiro Yamaguchi, Kamakura; Masakatsu Nakatsuka, Yokohama, all of Japan

[73] Assignee: Mitsui Toatsu Chemicals, Incorporated, Tokyo, Japan

[21] Appl. No.: 272,371

[22] Filed: Nov. 17, 1988

[30] Foreign Application Priority Data

Nov. 17, 1987 [JP] Japan ................... 62-288311
Dec. 16, 1987 [JP] Japan ................... 62-316019
Jan. 11, 1988 [JP] Japan ................... 63-002459
Jan. 13, 1988 [JP] Japan ................... 63-003685

[51] Int. Cl.$^5$ ............................................. G03G 5/06
[52] U.S. Cl. ........................................ 430/59; 430/73; 430/75
[58] Field of Search ...................... 430/59, 72, 73, 75

[56] References Cited

U.S. PATENT DOCUMENTS 4,808,503 2/1989 Yamada et al. ................. 430/73
4,833,054 5/1989 Akasaki et al. ................. 430/59

Primary Examiner—John L. Goodrow
Attorney, Agent, or Firm—Millen, White & Zelano

[57] ABSTRACT

There are here provided a novel tetraphenylthiophene derivative represented by the general formula

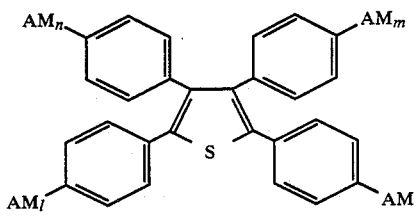

wherein AM is a tertiary amino group, each of l, m and n is the integer 0 or 1 and $1 \geq m \geq n$ are useful as the charge-transporting material in an electrophotographic photoreceptor having an electrically conductive base and a photosensitive layer thereon containing a charge-transporting material and a charge-generating material, which preferably is an azo compound.

13 Claims, 1 Drawing Sheet

P-AMINO SUBSTITUTED TETRAPHENYLTHIOPHENES AND ELECTROPHOTOGRAPHIC PHOTORECEPTORS CONTAINING THEM

BACKGROUND OF THE INVENTION (1) Field of the Invention

The present invention relates to novel p-amino substituted tetraphenylthiophenes and to electrophotographic photoreceptors containing them. More specifically, it relates to an electrophotographic photoreceptor in which a novel p-amino substituted tetraphenylthiophene is contained as a charge-transporting material in a photosensitive layer on an electrically conductive base.

(2) Description of the Prior Art

Heretofore, inorganic photosensitive materials such as selenium, cadmium sulfide and zinc oxide have been widely used as photosensitive materials for electrophotographic photoreceptors. However, the photoreceptors using such photosensitive materials do not sufficiently satisfy the requirements for electrophotographic photoreceptors such as sensitivity, light stability, moisture-proofness and durability. For example, the photoreceptors using selenium materials have excellent sensitivity but are susceptible to crystallization due to heat or contaminants, so that the characteristics of the photoreceptors deteriorate with use. In addition, this type of photoreceptors has many drawbacks, viz., manufacturing cost is high because of the utilization of vacuum evaporation and it is difficult to mold them into the form of a belt because of poor flexibility. The photoreceptors using the cadmium sulfide material have poor moisture-proofness and durability. Furthermore, the photoreceptors in which zinc oxide is used have unsatisfactory durability.

In order to eliminate these disadvantages of the photoreceptors using the inorganic photosensitive materials, various photoreceptors based on organic photosensitive materials have been investigated.

The photoreceptors developed to remove the above-mentioned drawbacks include function-separated photoreceptors in which a charge-generating function and a charge-transporting function are separately allocated to different materials. In the function-separated photoreceptors, materials having various desirable functions can be selected from a wide range of materials and combined with one another, which permits preparing photoreceptors having high sensitivity and sufficient durability.

Requirements for the charge-transporting material contained in the electrophotographic photoreceptor are as follows:

(1) Possess sufficiently high ability to receive electric charges generated from the charge-generating material.

(2) Capable of promptly transporting the received charges.

(3) Capable of successfully transporting the charges even in low electric field so that no charges remain.

In addition, the photoreceptor must be stable to light and heat during the repeating operation of electrification, exposure, development and transfer, and must have enough durability to obtain faithfully reproduced copy images.

As the charge-transporting materials, various compounds have been reported. For example, poly(N-vinylcarbazole) has been known for some time as a light-conductive material and photoreceptors in which this compound is used as the charge-transporting material have been put into practice. However, this type of photoreceptors has poor flexibility and is brittle, with the result that they readily crack. This fact means that their durability is so poor as to not withstand repeated use. Furthermore, when their flexibility is improved by the use of a binder, electrophotographic properties deteriorate.

Because low-molecular weight compounds have no coating properties, when a photosensitive layer is formed therewith, such a compound is mixed generally with a binder in an arbitrary ratio. Many charge-transporting materials have been suggested which comprise low-molecular weight compounds. For example, hydrazone compounds have high sensitivity as the charge-transporting material. (See Japanese Patent Publication Laid-open Nos. 55-46761, 55-52064, 57-58156 and 57-58157). However, these compounds tend to decompose by ozone generated during corona discharge and they are unstable to light and heat. In addition, when this kind of charge-transporting material is used, the thus-obtained images are poor in contrast or are fogged, owing to the degradation of charge retention ability by repeated use or owing to the accumulation of residual potential, even when initial performance is good.

Many other charge-transforming materials have been suggested but none of them sufficiently satisfy the practical requirements for use in an electrophotographic photoreceptor. Therefore, the development of better photoreceptors is desired.

OBJECTS OF THE INVENTION

An object of the present invention is to provide novel compounds which are useful as a charge-transporting material.

Another object of the present invention is to provide an electrophotographic photoreceptor having adequate sensitivity and excellent durability.

These and other objects of the present invention can be achieved by the use of a p-tert.-amino substituted tetraphenylthiophene as the charge-transporting agent in an electrophotographic photoreceptor.

SUMMARY OF THE INVENTION

The p-tert.-amino-substituted tetraphenylthiophenes of this invention can be represented by the general formula

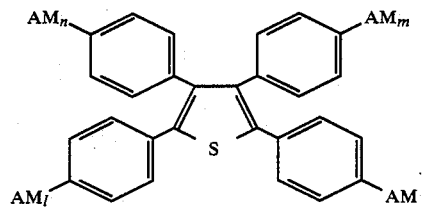

wherein each AM is a tertiary amino group, preferably of the formula $-NR_1R_2$ wherein each of $R_1$ and $R_2$ is an alkyl group, an aralkyl group or an aryl group or $R_1$ and $R_2$ together with the nitrogen atom form a heterocyclic amino group, each of l, m and n is the integer 0 or 1 and $l \geq m \geq n$.

The electrophotographic photoreceptors of this invention comprise an electrically conductive base and a photosensitive layer thereon containing a tetraphenylthiophene of the general formula (I) as a

DESCRIPTION OF THE PREFERRED EMBODIMENTS

Figure 1:
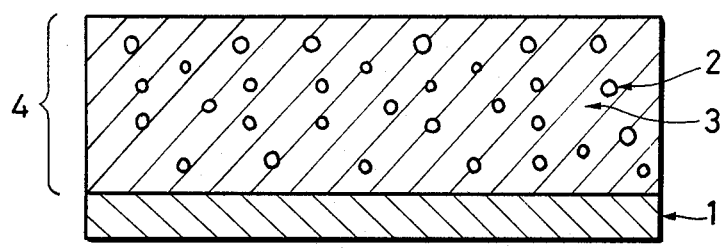
FIGS. 1 and 2 are cross-sectional views illustrating constitutional examples of electrophotographic photoreceptors.

In the p-tert.-amino substituted tetraphenylthiophenes of general formula (I), examples of $R_1$ and $R_2$ are those of 1 to 8 carbon atoms, which may be straight or branched chain, e.g., lower alkyl such as methyl, ethyl, isopropyl, butyl and octyl; examples of $R_1$ and $R_2$ aralkyl groups are carbocyclic aryl of 7 to 10 carbon atoms and 1 to 4 carbon atoms in the alkyl moiety, such as benzyl and phenethyl: and examples of $R_1$ and $R_2$ aryl groups are carbocyclic aryl of 6 carbon atoms, e.g., phenyl, naphthyl and biphenyl.

The $R_1$ and $R_2$ groups can be alike or different and one or more of them may bear one or more, e.g., 1, 2 or 3 simple substituents. Examples of substituents which can be present on an $R_1$ or $R_2$ group are halogen atoms, e.g., chlorine and bromine; hydrocarbon groups of 1 to 12 carbon atoms, including alkyl of 1 to 8 carbon atoms, e.g., lower alkyl such as methyl, ethyl, butyl and octyl; aralkyl groups of 7 to 10 carbon atoms, such as benzyl and phenethyl, and aryl groups, such as phenyl, biphenyl and naphthyl; an ether group including alkoxy groups of 1 to 5 carbon atoms, e.g., lower alkoxy such as methoxy, ethoxy, and butoxy; and an ester group including carboxylate groups of 1 to 6 carbon atoms, e.g., carbo-lower alkoxy, such as carbomethoxy and carboethoxy.

Examples of tertiary amino groups in which $R_1$ and $R_2$ are linked with the amino nitrogen atom to form a cycloalkyl amine include a pyrrolidino group and a piperidino group.

In the compounds of formula (1), preferably $R_1$ and $R_2$ both are aryl groups, since these compounds have high sensitivity and have excellent solubility in organic solvents.

The compounds represented by the above-mentioned general formula (I) can be synthesized, for example, by the following procedures:

(1) Reacting an amino compound represented by the general formula (V)

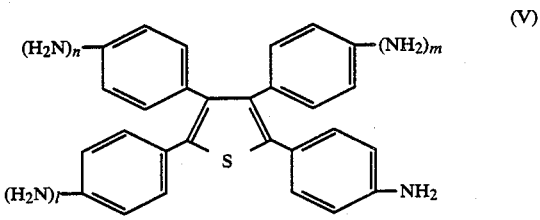

wherein each of l, m and n is the integer 0 to 1 $1 \geq m \geq n$, with an alkyl para-toluenesulfonate, dialkyl sulfate, and alcohol, an alkyl halide, aryl halide or like reagent reactive with a primary group. (2) Reacting a compound represented by the general formula (VI)

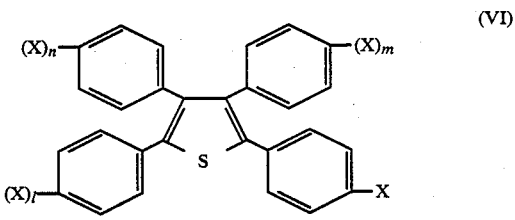

where in each of l, m and n is the integer 0 or 1 and $1 \geq m \geq n$, and X is a halogen atom, preferably an iodine atom, with an amine represented by the general formula (VII)

wherein $R_1$ and $R_2$ are as defined above.

Typical examples of compounds which can be used in the present invention are those recited in Table 1, which examples are illustrative and not restrictive.

TABLE 1

| Compound No. | l | m | n | $R_1$ | $R_2$ |
|---|---|---|---|---|---|
| 1 | 0 | 0 | 0 | phenyl | 4-methylphenyl |
| 2 | 0 | 0 | 0 | 4-methylphenyl | 4-methylphenyl |

TABLE 1-continued

[Structure: tetra(aminophenyl)-substituted thiophene with $R_1$, $R_2$ groups and indices $l$, $m$, $n$]

| Compound No. | l | m | n | $R_1$ | $R_2$ |
|---|---|---|---|---|---|
| 3 | 0 | 0 | 0 | phenyl | phenyl |
| 4 | 0 | 0 | 0 | 4-OCH$_3$-phenyl | 4-OCH$_3$-phenyl |
| 5 | 0 | 0 | 0 | 2,5-di(CH$_3$)-phenyl | 2-CH$_3$-5-OCH$_3$-phenyl |
| 6 | 0 | 0 | 0 | phenyl | 2-naphthyl |
| 7 | 1 | 0 | 0 | phenyl | 2-naphthyl |
| 8 | 1 | 0 | 0 | phenyl | phenyl |
| 9 | 1 | 0 | 0 | 4-Cl-phenyl | 4-Cl-phenyl |
| 10 | 1 | 0 | 0 | 4-CH$_3$-phenyl | 4-CH$_3$-phenyl |
| 11 | 1 | 0 | 0 | 4-OCH$_3$-phenyl | 4-OCH$_3$-phenyl |
| 12 | 1 | 0 | 0 | 4-COOC$_2$H$_5$-phenyl | 4-COOC$_2$H$_5$-phenyl |
| 13 | 1 | 0 | 0 | -CH$_2$-phenyl | -CH$_2$-phenyl |

TABLE 1-continued

| Compound No. | l | m | n | R₁ | R₂ |
|---|---|---|---|---|---|
| 14 | 1 | 0 | 0 | phenyl | 3-methyl-4-methoxyphenyl |
| 15 | 1 | 0 | 0 | 4-methylphenyl | 4-methylphenyl |
| 16 | 1 | 0 | 0 | 4-methylphenyl | phenyl |
| 17 | 1 | 0 | 0 | phenyl | 1-naphthyl |
| 18 | 1 | 0 | 0 | 1-naphthyl | 1-naphthyl |
| 19 | 1 | 0 | 0 | 3,4-dimethylphenyl | 3-methyl-4-methoxyphenyl |
| 20 | 1 | 1 | 0 | 4-methylphenyl | 4-methylphenyl |
| 21 | 1 | 1 | 0 | phenyl | phenyl |
| 22 | 1 | 1 | 0 | 2-chlorophenyl | 2-chlorophenyl |
| 23 | 1 | 1 | 0 | 4-($COOC_2H_5$)phenyl | 4-($COOC_2H_5$)phenyl |

TABLE 1-continued

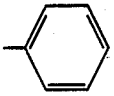

| Compound No. | l | m | n | R₁ | R₂ |
|---|---|---|---|---|---|
| 24 | 1 | 1 | 0 | 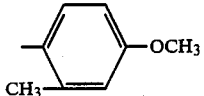 | 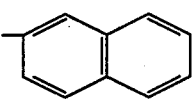 |
| 25 | 1 | 1 | 0 | 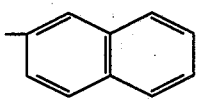 | 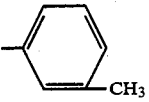 |
| 26 | 1 | 1 | 1 | 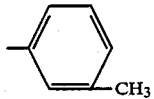 | 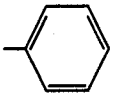 |
| 27 | 1 | 1 | 1 | 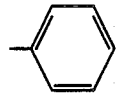 | 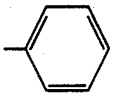 |
| 28 | 1 | 1 | 1 |  | 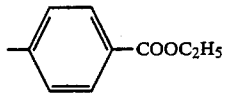 |
| 29 | 1 | 1 | 1 | 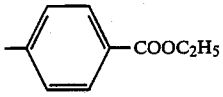 | 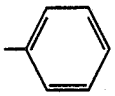 |
| 30 | 1 | 1 | 1 | 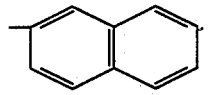 | 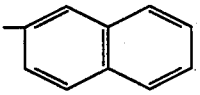 |
| 31 | 1 | 1 | 1 | 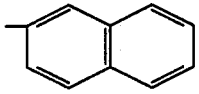 | |

A compound of the present invention, when used as a charge-transporting material in an electrophotographic photoreceptor, is combined with a charge-generating material.

Any material can be used as the charge-generating material, so long as it has an ability to generate an electric charge. Typical examples of charge-generating materials include inorganic materials such as selenium, selenium alloys, amorphous silicon and cadmium sulfide; and organic dyes and pigments of phthalocyanine, perylene, perynone, indigo, anthraquinone, cyanine, azo compounds, and the like. The phthalocyanine and azo compounds are especially suitable for the use as the charge-generating materials in combination with a charge-transporting material of the present invention.

Of the azo compound charge-generating materials which can impart to the electrophotographic photoreceptor excellent characteristics when employed in combination with a charge-transporting material of the present invention, compounds represented by one of the following formulae (II), (III) and (IV) are particularly preferred:

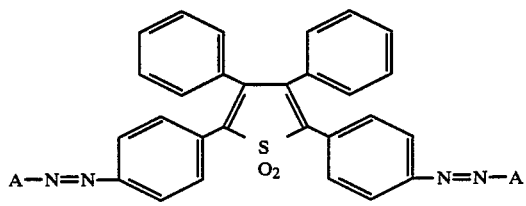

(II)

wherein A is a coupler residuum,

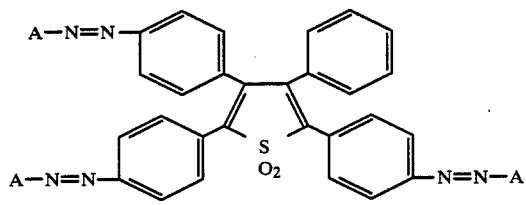

(III)

wherein A is a coupler residuum, and

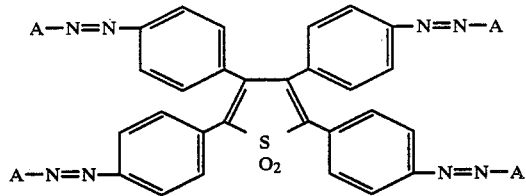

(IV)

wherein A is a coupler residuum.

The reason why a combination of one of these compounds and a charge-transporting material of this invention is particularly desirable could be due to various factors, but the advantages of the combination could not be predicted, based on the present technical level in this field. Therefore, the advantageous combination of a charge-transporting material of the present invention and an azo compound charge-generating material of formula (II), (III) or (IV) is also a surprising discovery.

Examples of the coupler residuum represented by the group A in the general formulae (II), (III) and (IV) include the following residua (a) to (d):

(a) Coupler residua having the general formula (VIII)

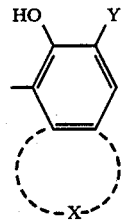

(VIII)

wherein X is a divalent bridging group which, with the benzene ring bearing the -OH and Y groups, forms a fused polycyclic carbocyclic or heterocyclic ring and Y is $-ON(R_4)-R_b{}_3$ or $-CONH.N=C(R_6)-R_5$ wherein $R_3$ is a hydrocarbon or a heterocyclic ring group, $R_4$ is a hydrogen atom, an alkyl group or a phenyl group, or $R_3$ and $R_4$ collectively with the nitrogen atom to which they are linked form a heterocyclic ring. $R_5$ is a hydrocarbon ring group, a heterocyclic ring group or a styryl group, $R_6$ is a hydrogen atom, an alkyl group or a phenyl group, or $R_5$ and $R_6$ collectively with the carbon atoms to which they are linked form a ring. Like $R_1$ and $R_2$, the X, $R_3$, $R_4$, $R_5$ and/or $R_6$ groups can have one or more simple substituents thereon.

Typical examples of rings formed by X in the general formula (VIII) include hydrocarbon rings such as naphthalene and anthracene, heterocyclic rings such as indole, carbazole, benzocarbazole and dibenzofuran, which are each condensed with the benzene ring bearing a hydroxyl group and Y.

When X bears a substituent, examples thereof include halogen atoms, such as chlorine and bromine, a hydroxyl group.

Examples of the cyclic $R_3$ and $R_5$ groups include carbocyclic rings such as phenyl, naphthyl, anthryl and pyrenyl; and heterocyclic rings such as pyridyl, thienyl, furyl, indolyl, benzofuranyl, carbazolyl and dibenzofuranyl. An example of a ring which can be formed collectively by R5 and $R_6$ is a fluorene ring.

When an $R_3$ or $R_5$ bears a substituent, examples thereof include alkyl groups such as methyl, ethyl butyl, alkoxy groups such as methoxy, ethoxy, propoxy and butoxy, halogen atoms such as chlorine and bromine, a halomethyl group such as trifluoromethyl, dialkylamino groups such as dimethylamino and diethylamino, nitro, cyano, carboxyl and esters, e.g., alkyl such as methyl and ethyl, thereof.

When $R_4$ or $R_6$ is a phenyl group, it also can bear a substituent, e.g., a halogen atom such as chlorine or bromine.

(b) Coupler residua having general formula (IX) and (X)

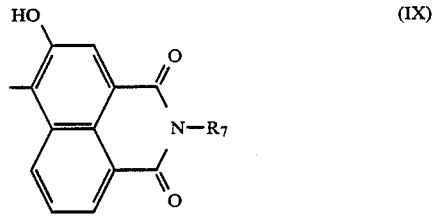

(IX)

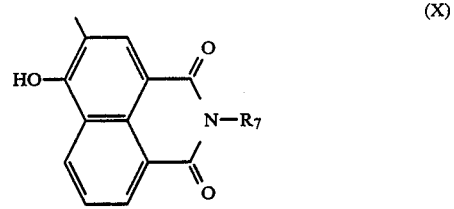

(X)

wherein $R_7$ is a hydrocarbon group, which may be substituted.

Examples of $R_7$ include alkyl groups as defined above for $R_1$and $R_2$, methyl, ethyl propyl, butyl and octyl and alkoxyalkyl groups, such as a methoxyethyl and an ethoxyethyl.

(c) Coupler residues having general formula (XI)

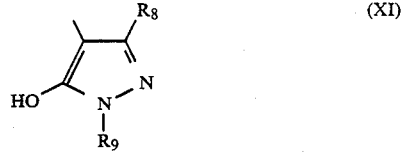

(XI)

wherein $R_8$ is an alkyl group, a carbamoyl group, a carboxy group or its ester, and $R_9$ is a carbocyclic ring group which may be substituted.

Examples of $R_9$ include hydrocarbon ring groups such as phenyl and naphthyl. Examples of substituents on the $R_9$ group are alkyl groups, such as methyl, ethyl, propyl and butyl, alkoxy groups, such as methoxy, ethoxy, propoxy, and butoxy, dialkylamino groups, such as a diethylamino and diethylamino, halogen atoms, such as chlorine and bromine, a nitro group and a cyano group.

(d) Coupler residues having general formula (XII) and (XIII)

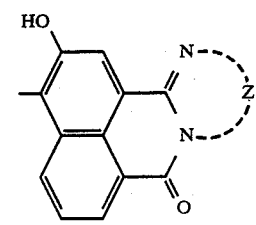
(XII)

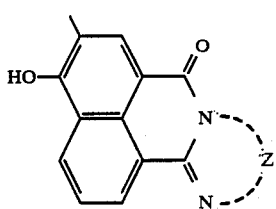
(XIII)

Wherein Z is a divalent hydrocarbon or heterocyclic ring groups, each of which may be substituted and which with the nitrogen atoms form a heterocyclic ring system.

Typical examples of Z include a divalent monocyclic aromatic hydrocarbon group such as o-phenylene, condensed polycyclic aromatic hydrocarbon groups, such as an o-naphthylene, peri-naphthylene, 1,2-anthraquinonylene and 9,10-phenanthrylene, and divalent heterocyclic ring groups, such as 3,4-pyrazoldiyl, 2,3-pyridinediyl, 4,5-pyrimidinediyl, 6,7-imidazolediyl, 5,6-benzimidazolediyl and 6,7-quinolinediyl. Examples of Z ring group substituents include alkyl groups, such as methyl, ethyl, propyl and butyl, alkoxy groups, such as methoxy, ethoxy, propoxy and butoxy, dialkylamino groups, such as dimethylamino and diethylamino, halogen atoms such as chlorine and bromine, a nitro group and a cyano group.

Of the coupler residua above recited, those which are represented by the general formula (VIII) are most preferable because they produce charge-generating azo compounds with high photosensitive properties and their intermediate raw materials are so readily available that the can be manufactured at low cost.

Typical examples of the coupler residues are as follows:

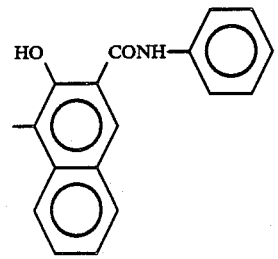
A-1

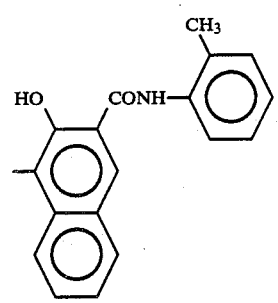
A-2

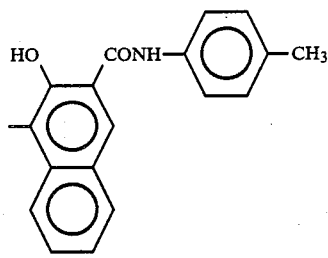
A-3

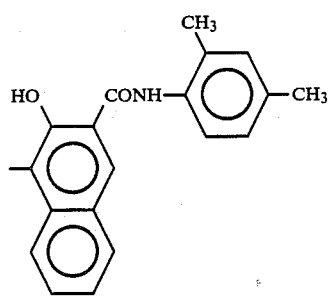
A-4

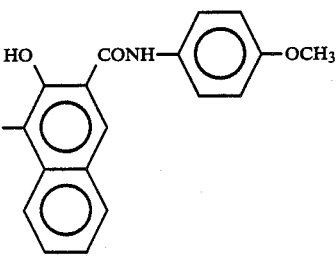
A-5

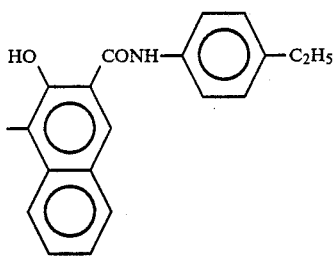
A-6

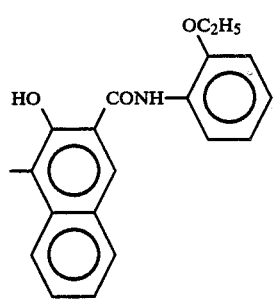 A-7
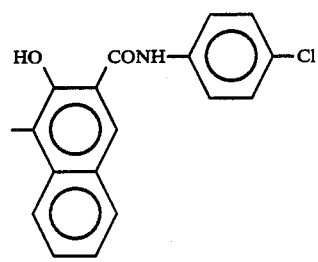 A-8
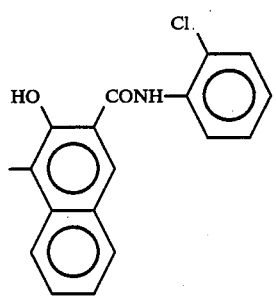 A-9
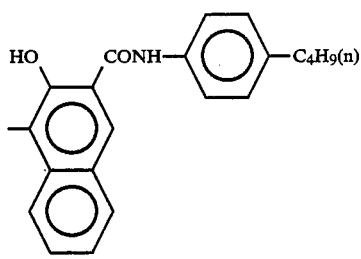 A-10
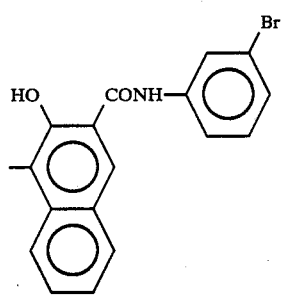 A-11
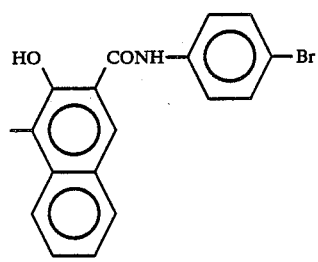 A-12
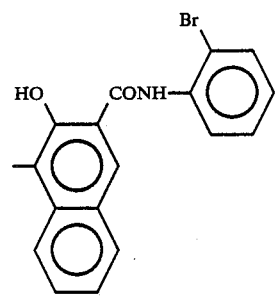 A-13
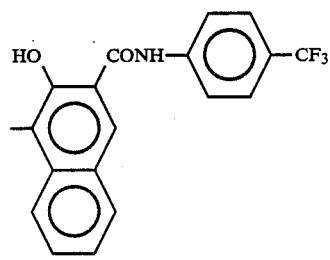 A-14
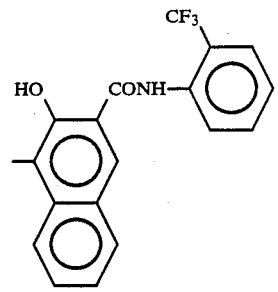 A-15
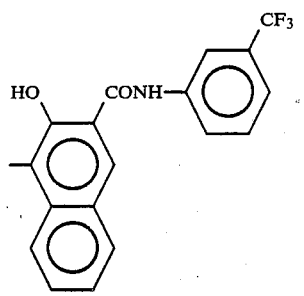 A-16

-continued
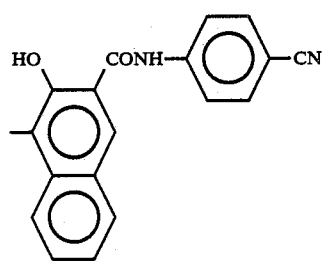 A-17
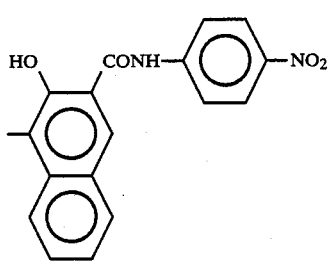 A-18
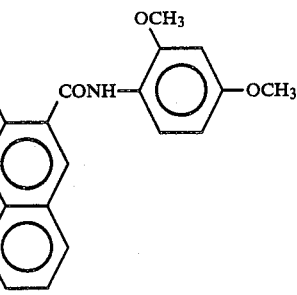 A-19
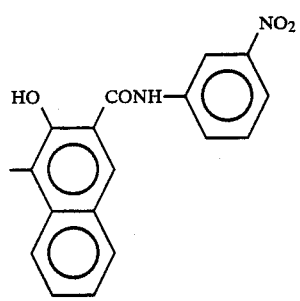 A-20
A-21
-continued
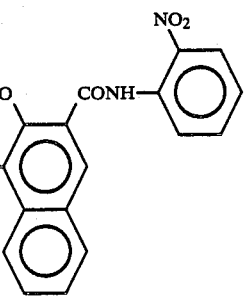 A-22
A-23
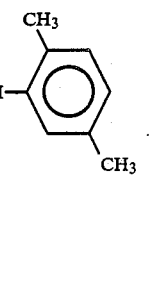 A-24
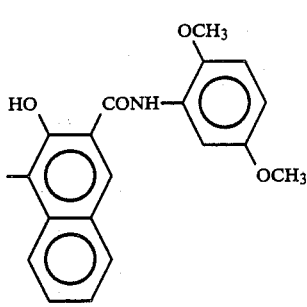 A-25
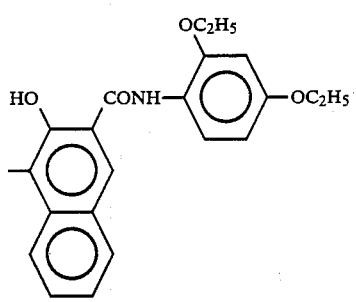 A-26

-continued
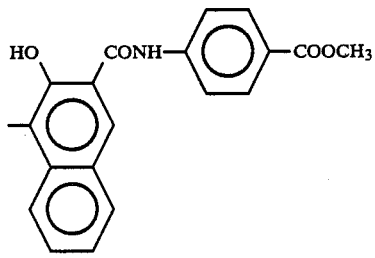 A-27
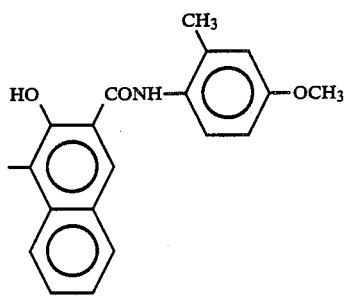 A-32
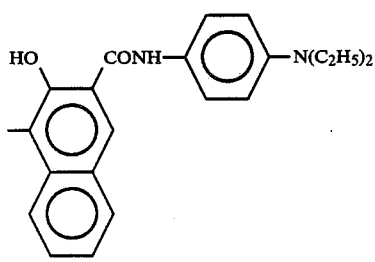 A-28
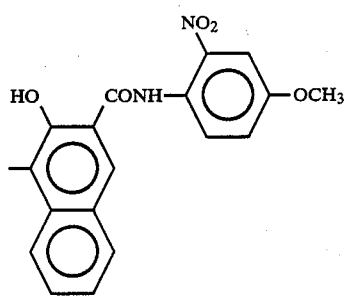 A-33
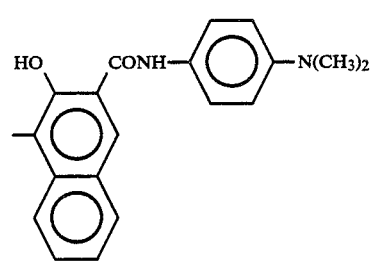 A-29
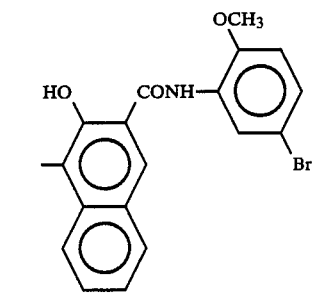 A-34
A-30
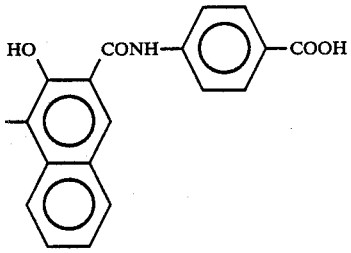 A-35
A-31
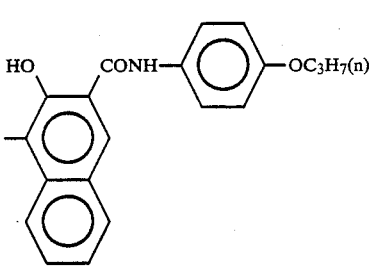 A-36

-continued
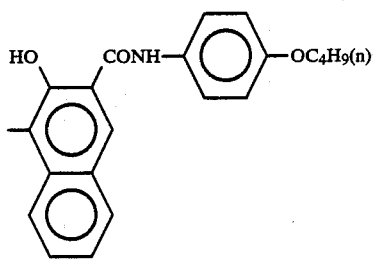
A-37
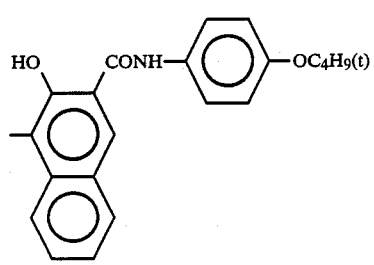
A-38
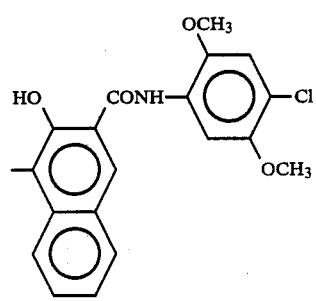
A-39
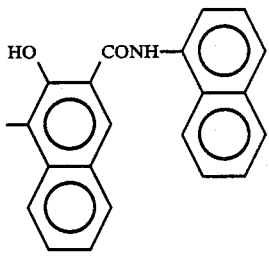
A-40
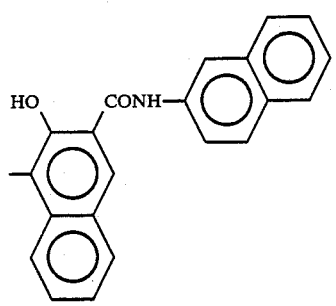
A-41
-continued
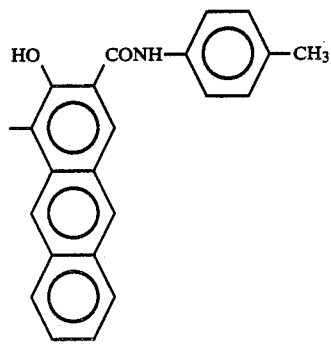
A-42
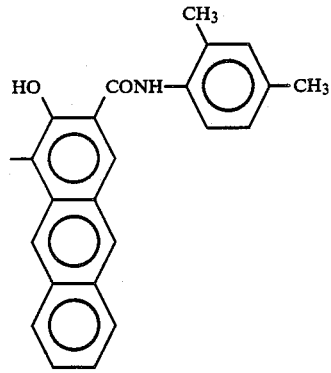
A-43
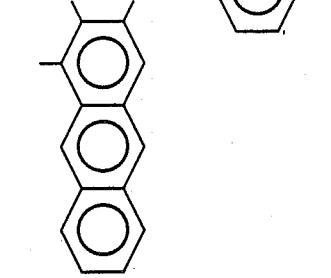
A-44
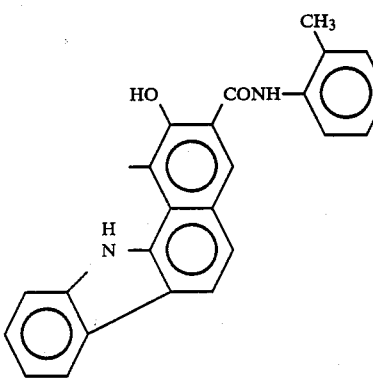
A-45

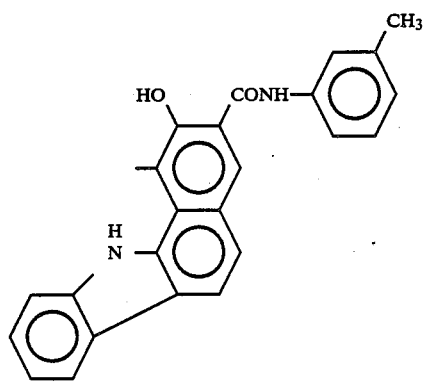
A-46
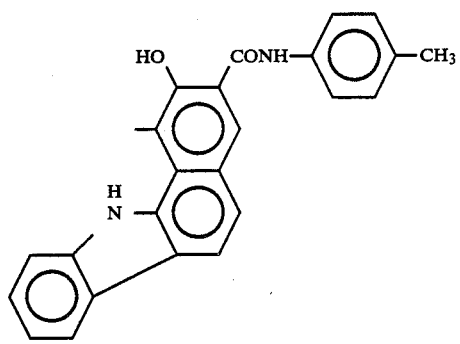
A-47
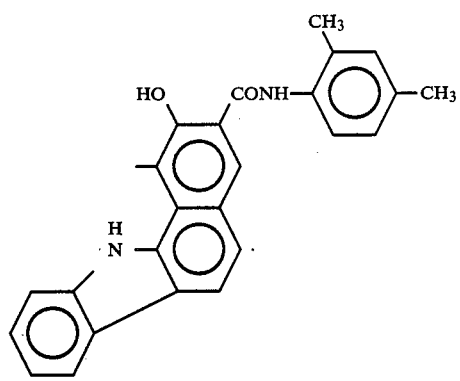
A-48
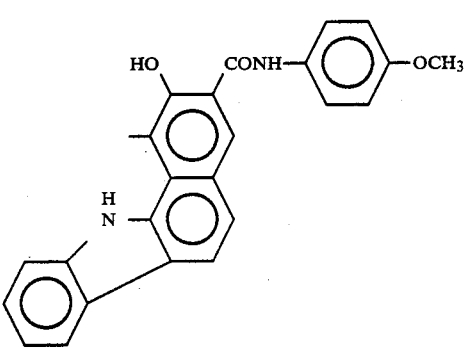
A-49
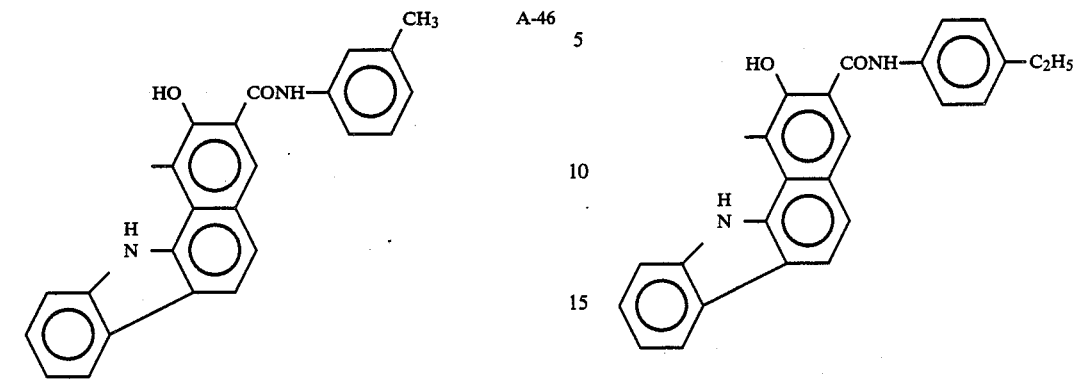
A-50
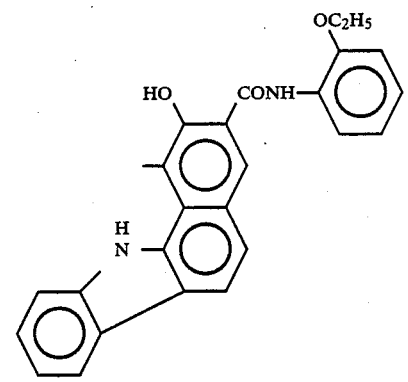
A-51
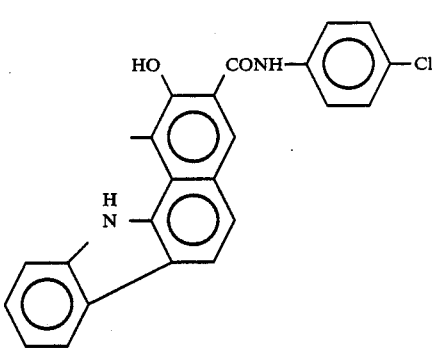
A-52
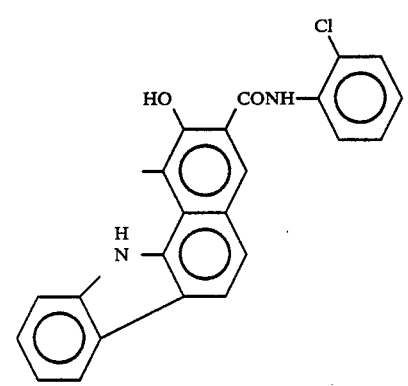
A-53

-continued
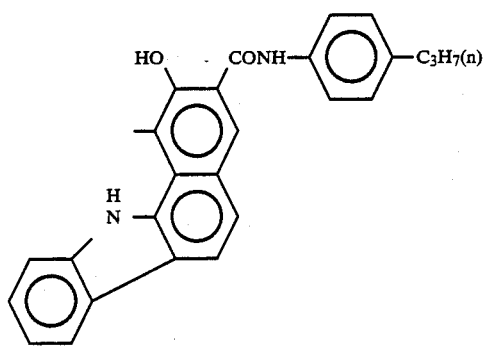
A-54
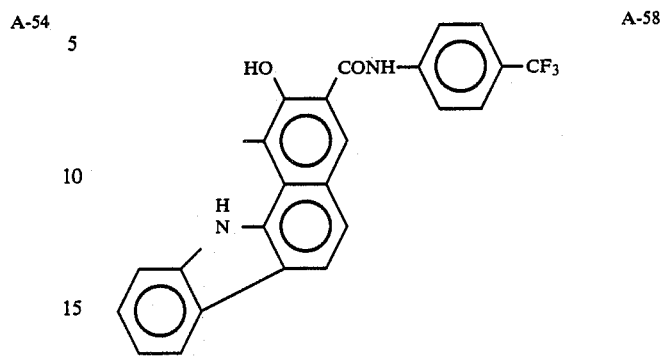
A-58
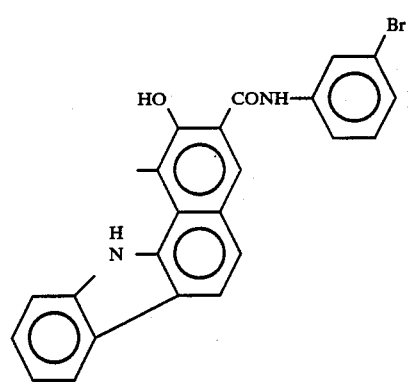
A-55
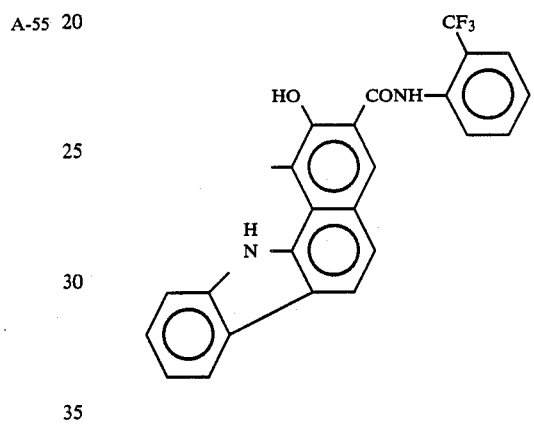
A-59
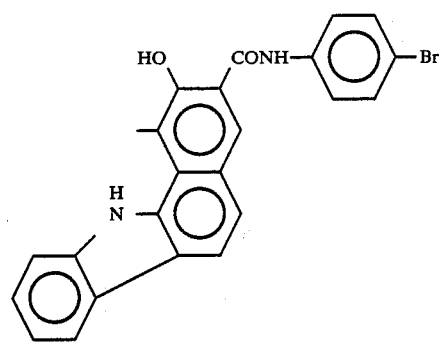
A-56
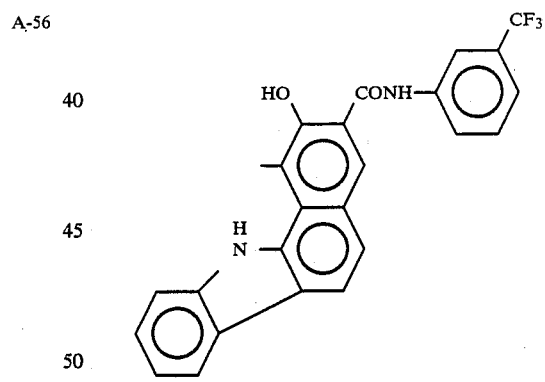
A-60
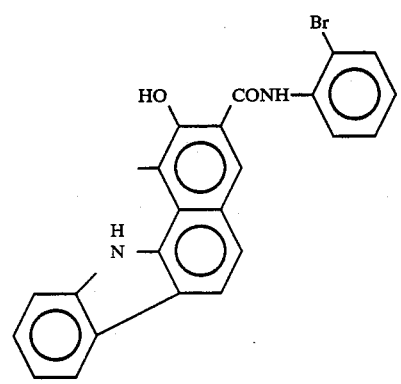
A-57
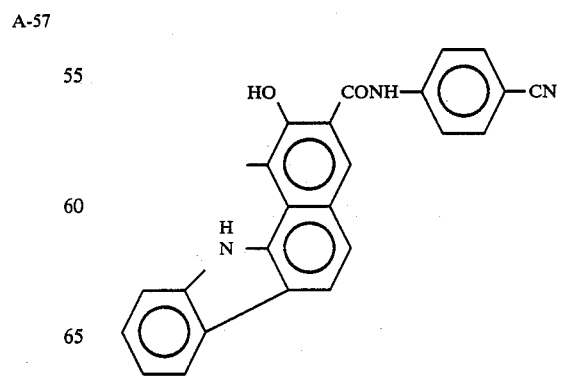
A-61

-continued
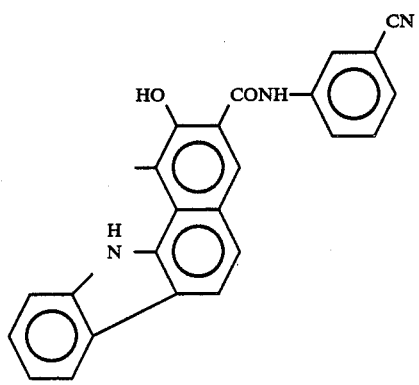 A-62
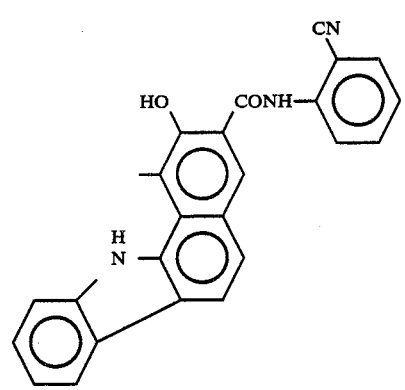 A-63
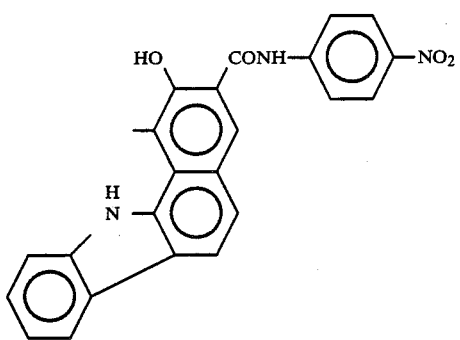 A-64
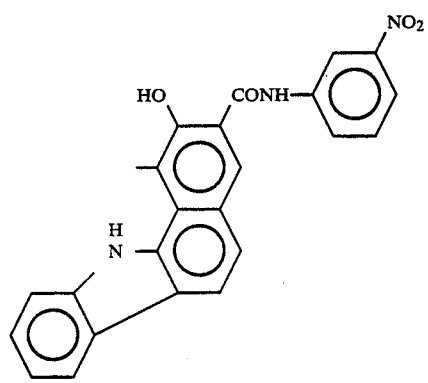 A-65
-continued
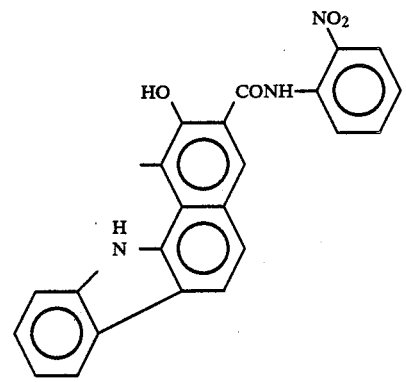 A-66
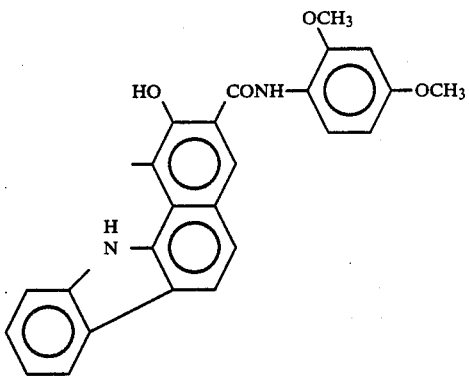 A-67
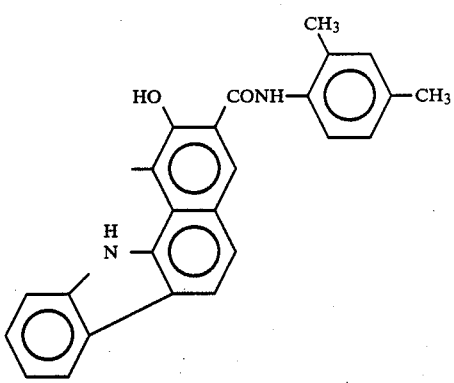 A-68
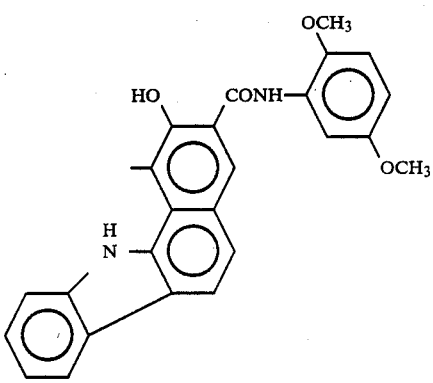 A-69

-continued
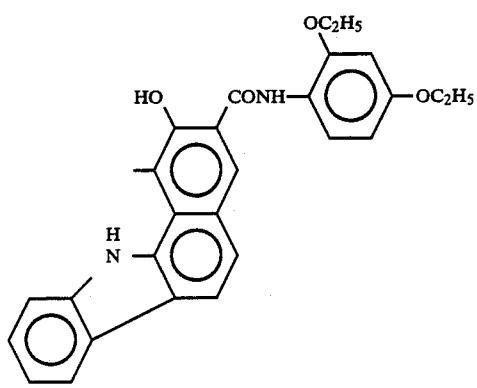 A-70
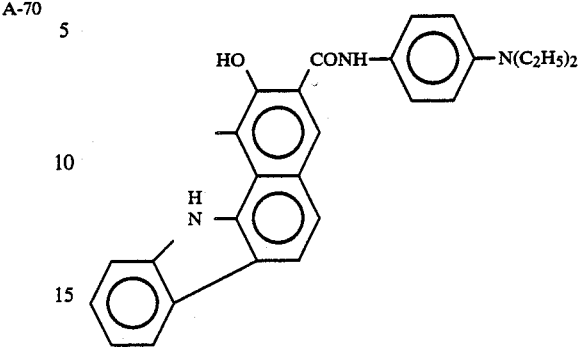 A-74
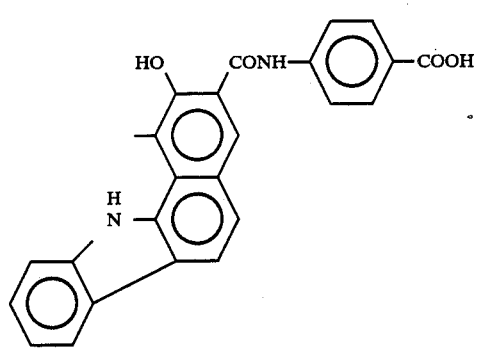 A-71
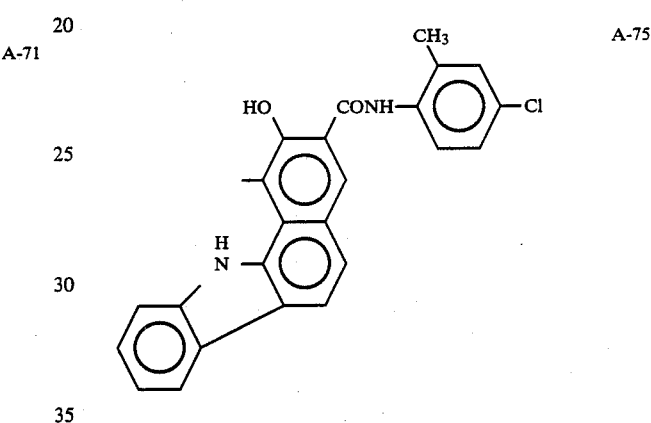 A-75
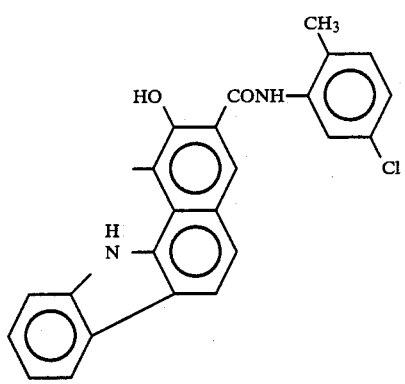 A-72
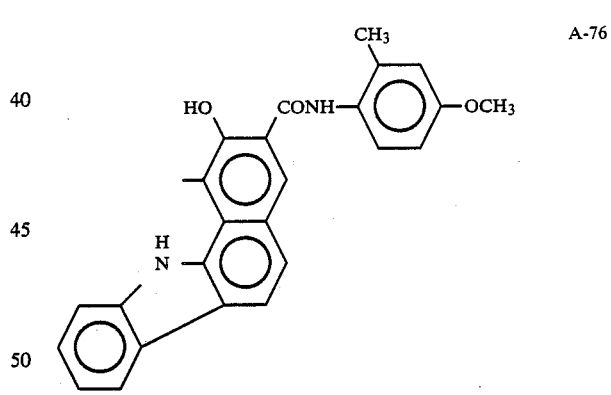 A-76
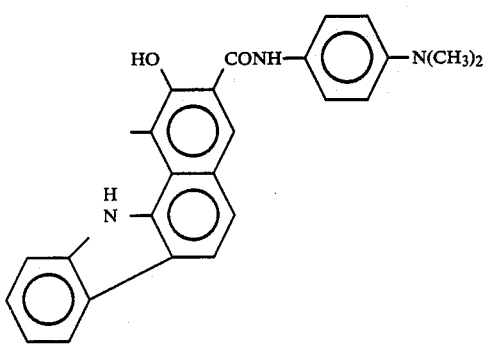 A-73
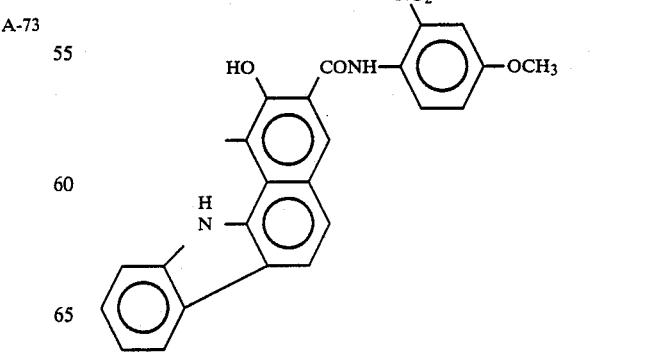 A-77

-continued
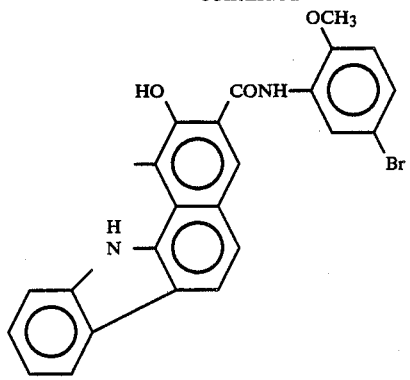 A-78
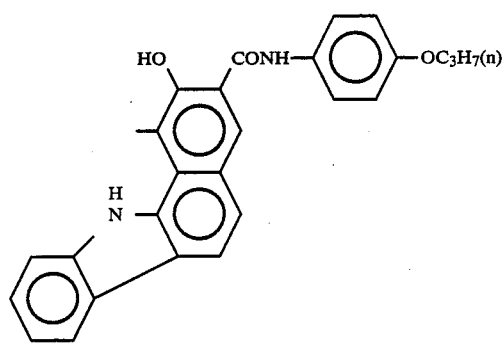 A-79
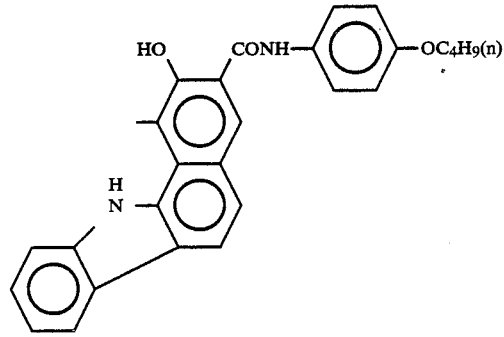 A-80
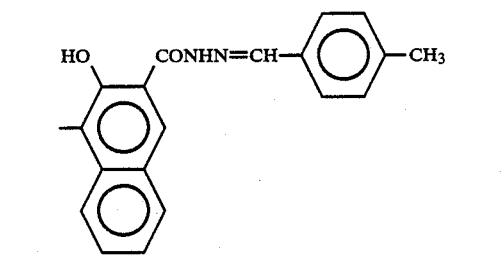 A-81
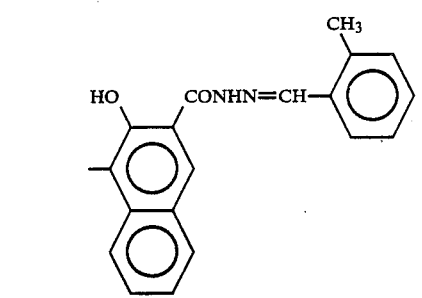 A-82
-continued
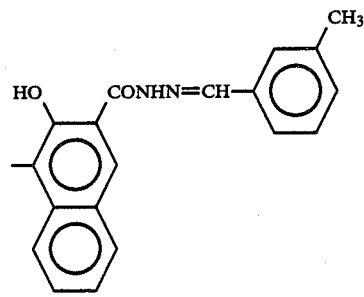 A-83
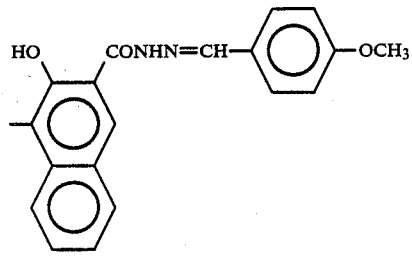 A-84
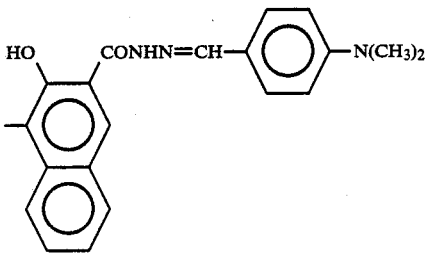 A-85
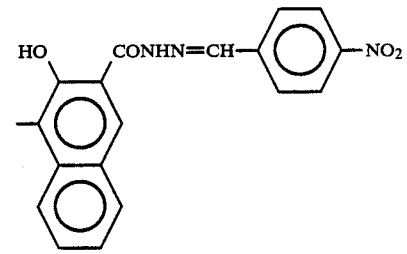 A-86
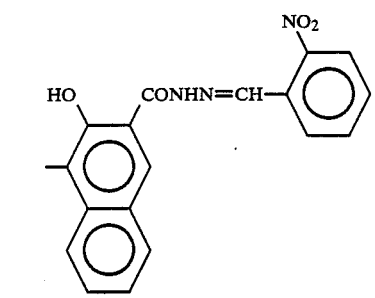 A-87

-continued
A-88
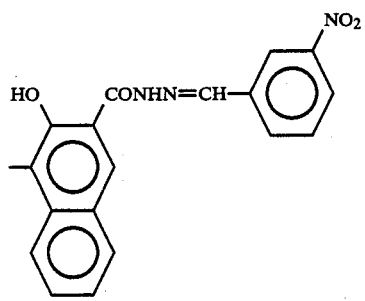
A-89
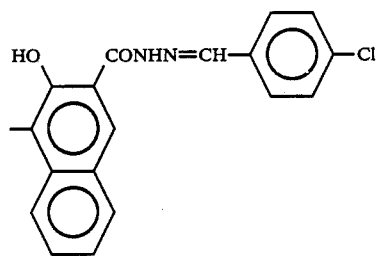
A-90
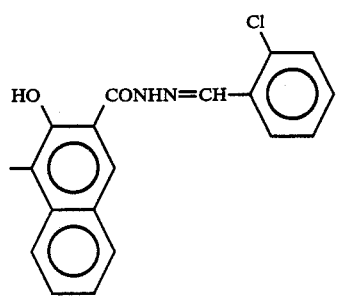
A-91
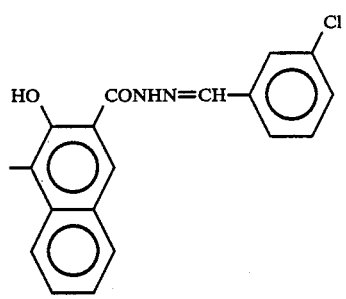
A-92
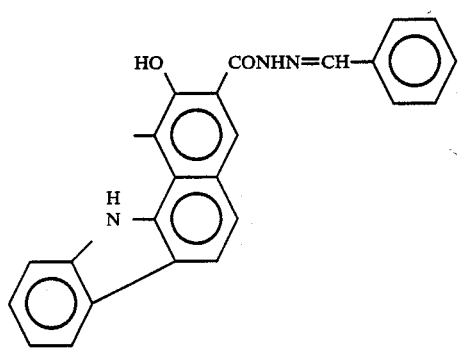
-continued
A-93
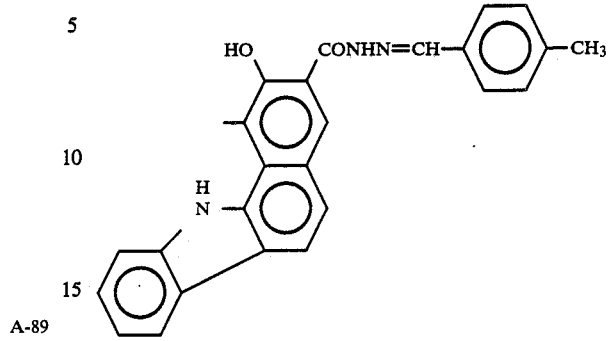
A-94
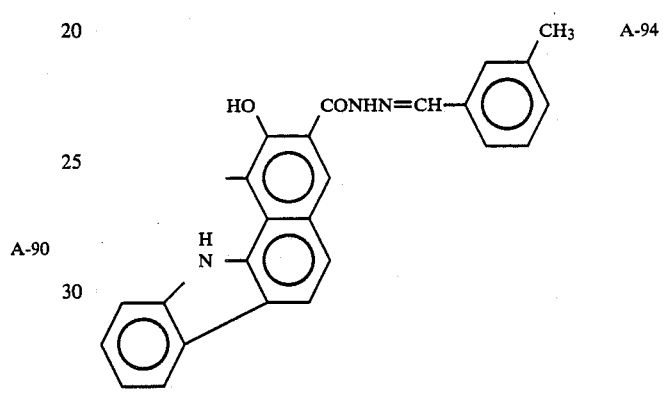
A-95
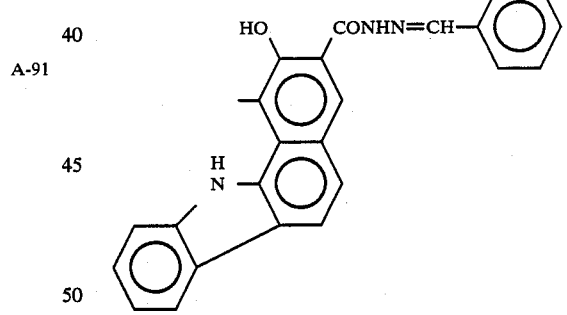
A-96
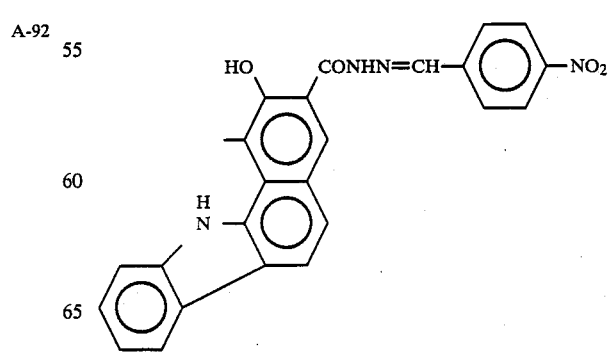

-continued
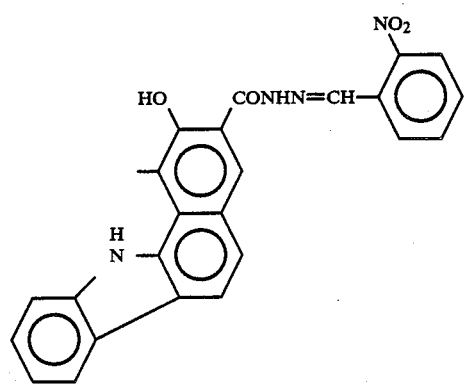
A-97
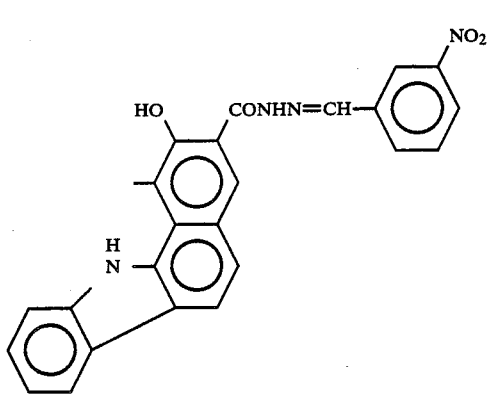
A-98
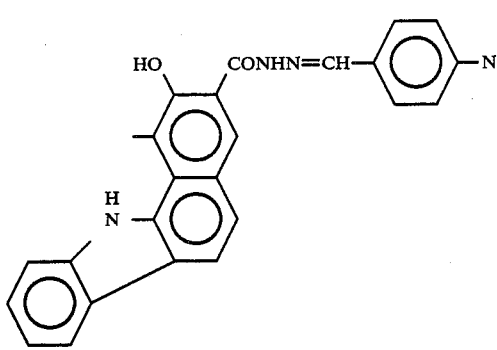
A-99
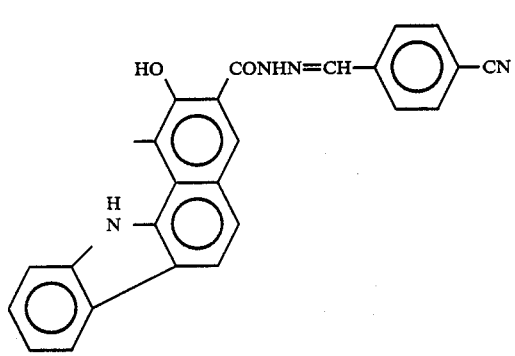
A-100
-continued
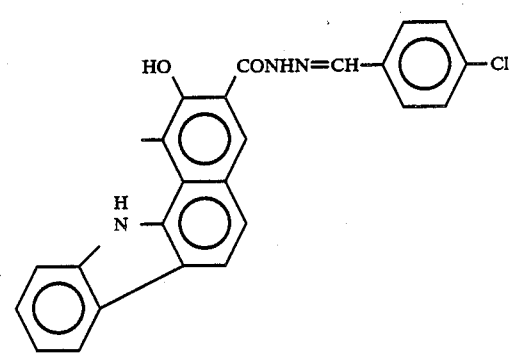
A-101
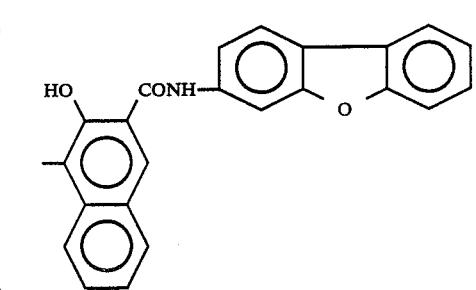
A-102
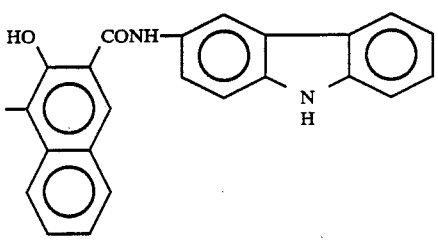
A-103
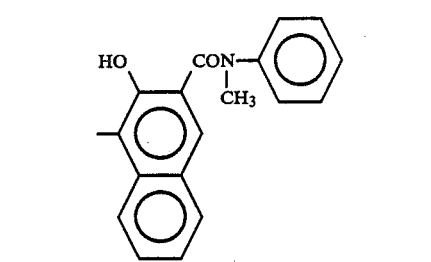
A-104
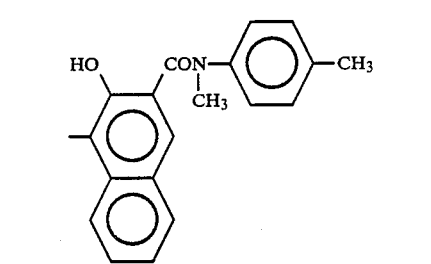
A-105

-continued

A-106, A-107, A-108, A-109, A-110, A-111, A-112, A-113, A-114

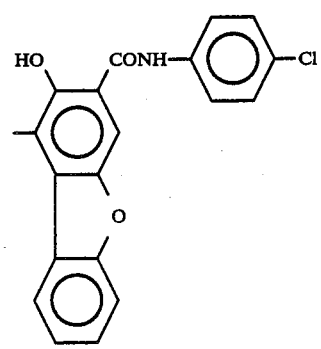 A-115
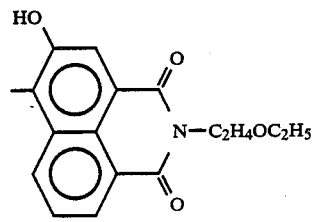 A-121
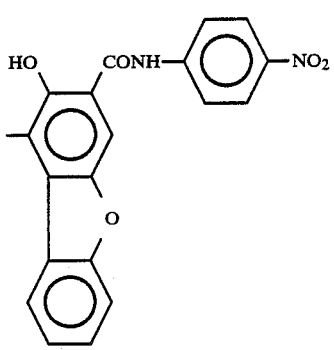 A-116
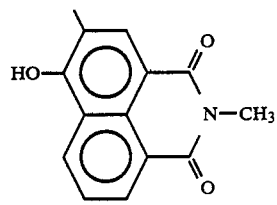 A-122
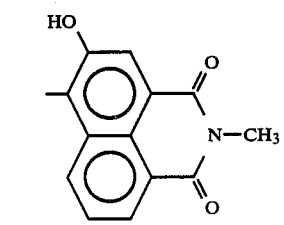 A-117
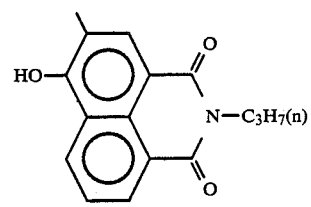 A-123
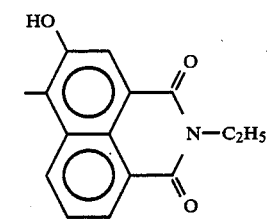 A-118
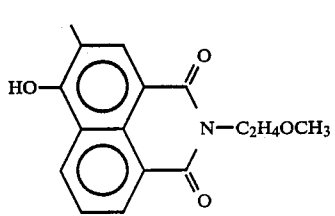 A-124
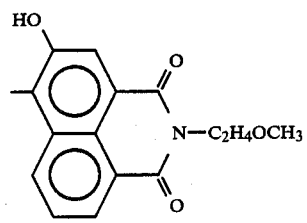 A-119
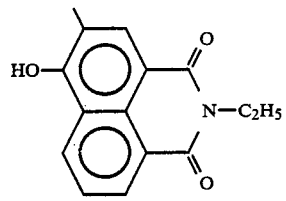 A-125
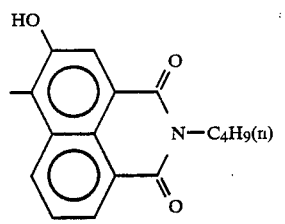 A-120
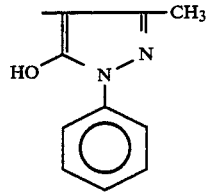 A-126
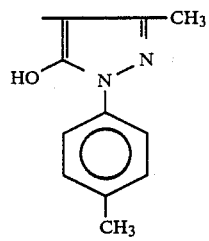 A-127

A-128 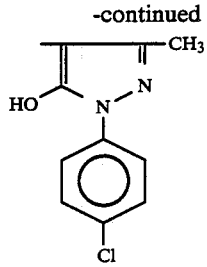
A-129 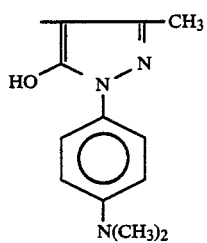
A-130 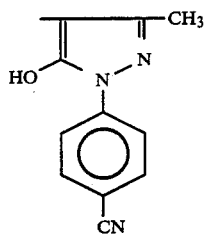
A-131 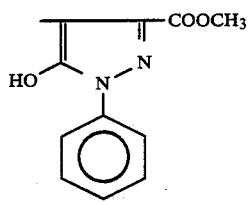
A-132 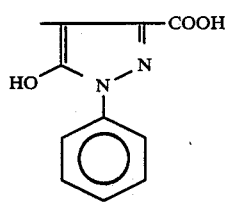
A-133 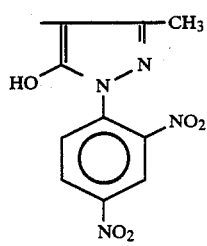
A-134 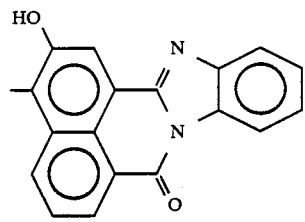
A-135 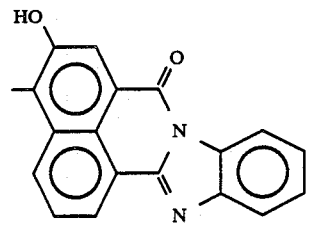
A-136 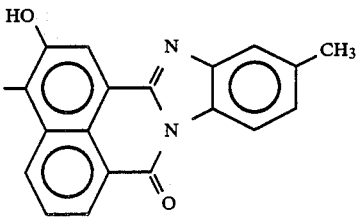
A-137 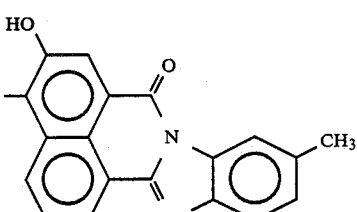
A-138 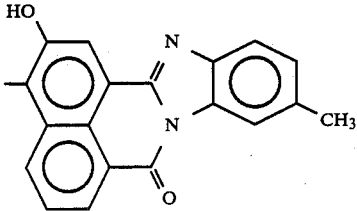
A-139 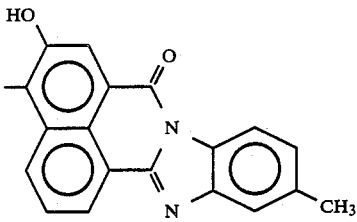
A-140 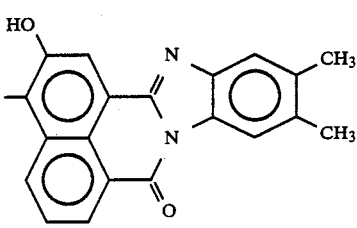
A-141 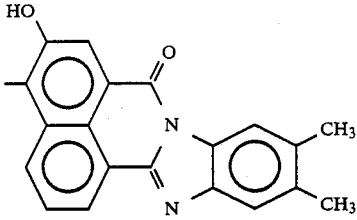

-continued

A-142
A-143
A-144
A-145
A-146
A-147
A-148
A-149
A-150
A-151
A-152
A-153

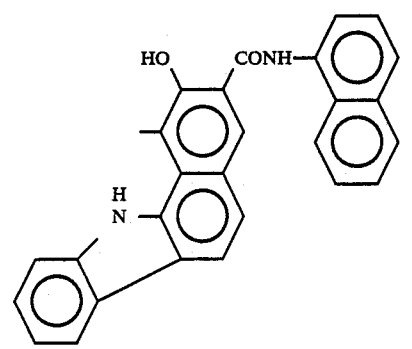

A-154

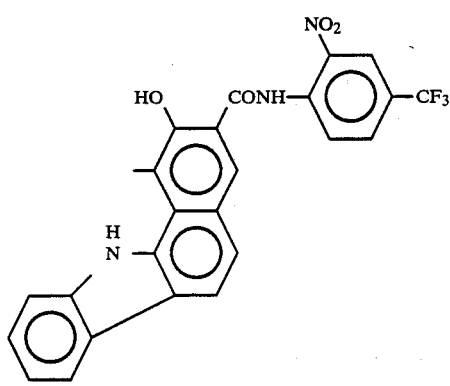

A-155

The azo compounds represented by the general formula (II), (III) and (IV) can be manufactured by, for example, a method disclosed in EP No. 0270685.

The compound of the present invention has no ability to provide coating films by itself, and therefore it is used together with a binder in order to form a photosensitive layer. As the binder, an insulating polymer can be employed. Examples of the insulating polymer include polystyrene, polyacrylamide, polyvinyl chloride, polyester resins, polycarbonate resins, epoxy resins, phenoxy resins and polyamide resins. In particular, the polyester resins and polycarbonate resins can be suitably used. In addition, poly-N-vinylcarbazole which has charge-transporting ability by itself can be also employed.

Figure 2:
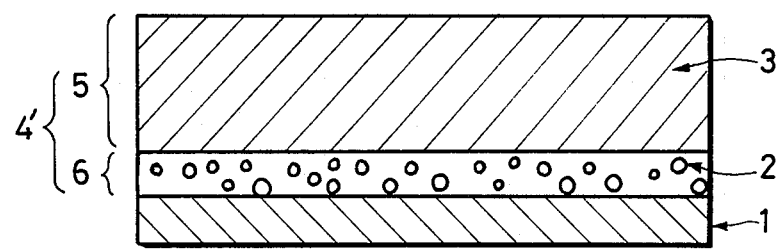

The photoreceptor may be in the form of a constitution in which a photosensitive layer 4 containing a charge-generating material 2 and a charge-transporting material 3 is superposed upon an electrically conductive base 1, as shown in FIG. 1; a constitution in which a photosensitive layer 4' is superposed upon the electrically conductive base 1, the photosensitive layer 4' being composed of a charge-generating layer 6 containing the charge-generating material 2 and a charge-transporting layer 5 containing the charge transporting material 3 thereon, as shown in FIG. 2; and a constitution in which the charge-generating layer 6 and the charge-transporting layer 5 in FIG. 2 are inversely disposed. The photoreceptor having any one of the above-mentioned constitutions is effective in the present invention, but the laminate type photoreceptor shown in FIG. 2 is preferable in that excellent electrophotographic characteristics can be obtained.

The constitution of the photoreceptor will be further described in detail in reference to FIG. 2.

Examples of usable raw materials for the electrically conductive base 1 include metallic plates of aluminum, copper and zinc; those which have been prepared by depositing conductive materials such as aluminum and $SnO_2$ on plastic sheets or films of polyester and the like; and papers or resins which have been rendered conductive.

The charge-generating layer 6 can be formed from the above-mentioned charge-generating material 2 in accordance with a method of vacuum-evaporating the charge-generating material 2 on the electrically conductive base 1, a method of applying and drying a solution containing the charge-generating material 2, a method of applying and drying a dispersion in which fine particles of the charge-generating material 2 are dispersed, or another method.

The thickness of the charge-generating layer 6 is in the range of 0.01 to 5 μm, preferably 0.05 to 2 μm. When this thickness is less than 0.01 μm, the generation of the charge is insufficient, and when it is more than 5 μm, residual potential is high, which is practically unpreferable.

The charge-transporting layer 5 may be formed by dissolving the compound of the present invention and the above-mentioned binder in a suitable solvent, and then applying and drying the mixture. In the charge-transporting layer 5, the charge-transporting material 3 is contained in an amount of 10 to 95% by weight, preferably 30 to 90% by weight. When the charge-transporting material 3 is less than 10% by weight, the charge is scarcely transported, and when it is more than 95% by weight, mechanical strength of the photoreceptor is poor, which is practically unpreferable.

The thickness of the charge-transporting layer 5 is preferably in the range of 3 to 50 μm, more preferably 5 to 30 μm. When this thickness is less than 3 μm, electrification quantity is insufficient, and when it is more than 50 μm, residual potential is high, which is practically unpreferable.

Between the photosensitive layer and the electrically conductive base, an intermediate layer may be interposed. Suitable examples of raw materials for the intermediate layer include polyamide, nitrocellulose, casein and polyvinyl alcohol, and the thickness of the intermediate layer is preferably 1 μm or less.

As described above, the electrophotographic photoreceptor of the present invention may be composed of the compound represented by the general formula (I), the electrically conductive base, the charge-generating material and the binder, but other constitutional elements of the photoreceptor may be additionally used, so long as they have functions as such elements.

In the electrophotographic photoreceptor of the present invention, a novel compound represented by the general formula (I) is used as the charge-transporting material, and therefore this photoreceptor has high sensitivity, sufficient durability to repeating use, and other excellent advantages.

Now, the present invention will be described in detail by way of examples, but the scope of the present invention should not be limited to these examples.

PREPARATION EXAMPLE 1

(Synthesis of Exemplary Compound No. 7)

In 50 ml of sulfolane were dispersed 12 g of 2,5-bis(4-iodophenyl)-3,4-diphenylthiophene, 10 g of N-phenyl-2naphthylamine, 10 g of anhydrous potassium carbonate and 8 g of electrolytic copper, and the mixture was then stirred at 190° C. for 40 hours. After standing, the mixture was added to 100 ml of water, and the resultant precipitate was collected by filtration and was then washed with water and methanol in this order, followed by drying. The thus obtained crude product was extracted with benzene, and the extract was purified through a silica gel column chromatography using a mixed solvent of benzene and hexane (1:1) as a developing solution. By recrystallization from a mixed solvent of benzene and acetonitrile, 15 g of light-yellow crystals (melting point=145° to 146° C.) was obtained.

It was confirmed by elemental analysis that the product was Exemplary Compound No. 7.

| | Results of Elemental Analysis (%) | | | |
|---|---|---|---|---|
| | C | H | N | S |
| Calcd. | 87.56 | 5.14 | 3.40 | 3.90 |
| Found | 87.34 | 5.08 | 3.31 | 4.04 |

PREPARATION EXAMPLE 2

(Synthesis of Exemplary Compound No. 3)

In 200 ml of orthodichlorobenzene (hereinafter referred to simply as ODCB) was dissolved 4.1 g of 2-(4-aminophenyl)3,4,5-triphenylthiophene, and to the mixture were added 5.1 g of iodobenzene, 11 g of anhydrous potassium carbonate, 2.6 g of electrolytic copper and 0.6 g of 18-crown-6-ether. In a nitrogen atmosphere, the mixture was then heated under reflux with vigorous stirring for 48 hours. A solid was collected by filtration, and afterward ODCB was distilled off from the reaction solution by means of steam distillation. The thus obtained residue was purified through a silica gel column chromatograph using benzene as a developing solution. Afterward, by recrystallization from a mixed solvent of benzene and hexane (1:1), 2.5 g of light-yellow crystals (melting point=225.0° to 228.8° C.) was obtained.

It was confirmed by elemental analysis that the product was Exemplary Compound No. 3.

| | Results of Elemental Analysis (%) | | | |
|---|---|---|---|---|
| | C | H | N | S |
| Calcd. | 86.45 | 5.26 | 2.52 | 5.77 |
| Found | 86.15 | 5.00 | 2.80 | 6.05 |

PREPARATION EXAMPLE 3

(Synthesis of Exemplary Compound No. 4)

The same procedure as in Preparation Example 2 was conducted with the exception that 4.1 g of 2-(4-aminophenyl)-3,4,5-triphenylthiophene and 8.2 g of p-iodoanisole were used, to obtain 3 g of yellow crystals (melting point=132.8° to 134.6° C.).

It was then confirmed by elemental analysis that the product was Exemplary Compound No. 4.

| | Results of Elemental Analysis (%) | | | |
|---|---|---|---|---|
| | C | H | N | S |
| Calcd. | 81.92 | 5.40 | 2.27 | 5.20 |
| Found | 81.90 | 5.19 | 2.16 | 4.91 |

PREPARATION EXAMPLE 4

(Synthesis of Exemplary Compound No. 8)

The same procedure as in Preparation Example 2 was conducted with the exception that 4.2 g of 2,5-bis(4-aminophenyl)-3,4-diphenylthiophene and 12.5 g of iodobenzene were used, to obtain 4 g of light-yellow crystals [melting point=126° to 129° C.; λmax=370 nm (CHCl$_3$)].

It was then confirmed by elemental analysis that the product was Exemplary Compound No. 8.

| | Results of Elemental Analysis (%) | | | |
|---|---|---|---|---|
| | C | H | N | S |
| Calcd. | 86.39 | 5.30 | 3.88 | 4.43 |
| Found | 86.29 | 4.94 | 3.85 | 4.18 |

PREPARATION EXAMPLE 5

(Synthesis of Exemplary Compound No. 10)

The same procedure as in Preparation Example 2 was conducted with the exception that 4.2 g of 2,5-bis(4-aminophenyl)-3,4-diphenylthiophene and 13.2 g of p-iodotoluene were used, to obtain 4 g of yellow crystals (melting point=241.4° to 243.3° C.). It was then confirmed by elemental analysis that the product was Exemplary Compound No. 10.

| | Results of Elemental Analysis (%) | | | |
|---|---|---|---|---|
| | C | H | N | S |
| Calcd. | 86.34 | 5.95 | 3.60 | 4.12 |
| Found | 86.30 | 5.93 | 3.52 | 4.10 |

PREPARATION EXAMPLE 6

(Synthesis of Exemplary Compound No. 21)

The same procedure as in Preparation Example 2 was conducted with the exception that 4.3 g of 2,3,5-tris(4-aminophenyl)-4-phenylthiophene and 18.5 g of iodobenzene were used, to obtain 4 g of yellow crystals [melting point=238° C.; to 242° C.; λmax=373 nm (CHCl$_3$)].

It was then confirmed by elemental analysis and from a molecular ion peak at 889(M+) in FD-MASS that the product was Exemplary Compound No. 21.

| | Results of Elemental Analysis (%) | | | |
|---|---|---|---|---|
| | C | H | N | S |
| Calcd. | 86.36 | 5.32 | 4.72 | 3.60 |
| Found | 86.82 | 5.22 | 4.52 | 3.38 |

PREPARATION EXAMPLE 7

(Synthesis of Exemplary Compound No. 27)

The same procedure as in Preparation Example 2 was conducted with the exception that 4.3 g of tetrakis(4-aminophenyl)thiophene and 24.5 g of iodobenzene were used, to obtain 6 g of yellow crystals [melting point=228° to 232° C.; λmax=375 nm (CHCl$_3$)].

It was then confirmed by elemental analysis and from a molecular ion peak at 889(M+) in FD-MASS that the product was Exemplary Compound No. 27.

| | Results of Elemental Analysis (%) | | | |
|---|---|---|---|---|
| | C | H | N | S |
| Calcd. | 86.33 | 5.34 | 5.30 | 3.03 |
| Found | 86.62 | 5.08 | 5.04 | 2.89 |

EXAMPLE 1

In a ball mill, 0.5 g of polyester resin (made by Toyobo Co., Ltd.; trade name "Bylon 200"), 0.5 g of a diazo dye (CG-1) represented by the structural formula

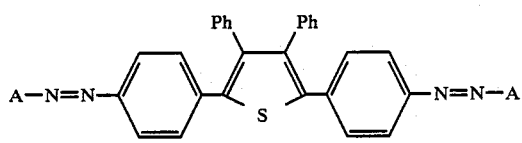

p wherein A is a group having the formula

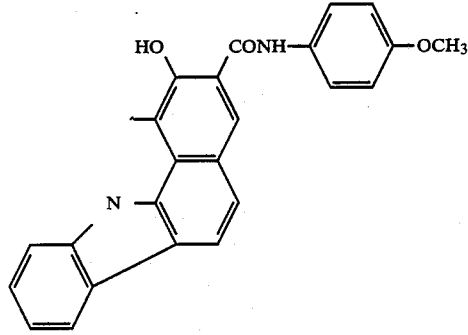

and Ph is a phenyl group, and 50 g of tetrahydrofuran were ground and mixed, and an aluminum plate was coated with the obtained dispersion by the use of a wire bar. Afterward, the coated plate was dried at 80° C. for 20 minutes to form a charge-generating layer having a thickness of about 0.5 μm.

This charge-generating layer was then coated by the use of a wire bar with a solution in which 1 g of Exemplary Compound No. 8, 1 g of polyester resin (trade name "Bylon 200"; made by Toyobo Co., Ltd.) were dissolved in 10 g of chloroform. The layer was afterward dried at 80° C. for 30 minutes to form a charge-transporting layer thereon having a thickness of about 18 μm, thereby preparing a laminate type photoreceptor as shown in FIG. 2.

The photoreceptor was electrified by corona discharge of 6 KV from an electrostatic copy paper test device (made by Kawaguchi Denki Seisakujo Co., Ltd.; model EPA-No. 8100), and at this time, surface potential VO was measured. Afterward, the photoreceptor was allowed to stand in a dark place for 2 seconds, and at this time, a surface potential $V_2$ was measured. In succession, the specimen was irradiated with light from a halogen lamp (color temperature=2,856° K.) so that the surface illuminance of the photoreceptor might be 5 lux, and a period of time which was taken until the surface potential attained a level of ½ of $V_2$ was measured. From measurements, the value of a half-life exposure $E_{\frac{1}{2}}$ (lux·sec) was then calculated. Furthermore, after 10 seconds were elapsed from the start of the light irradiation, a surface potential $V_{12}$, i.e., a residual potential was measured. Afterward, the operation of an electrification and an exposure were repeated 1,000 times.

EXAMPLES 2 to 6

The same procedure as in Example 1 was repeated with the exception that charge-transporting materials were changed to prepare photoreceptors, and measurements were done for the same items. The used charge-transporting materials and the measured results are set forth in Table 2.

EXAMPLE 7

The same procedure as in Example 1 was conducted with the exception that a diazo dye (CG-2) represented by the following structural formula was used as a charge-generating material to prepare a photoreceptor, and measurements were done for the same items:

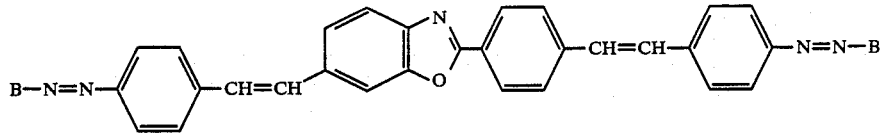

wherein B is a group having the formula:

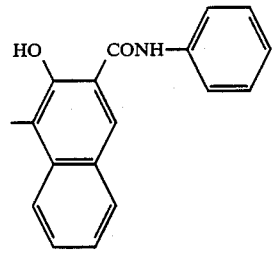

EXAMPLES 8 to 12

The same procedure as in Example 2 was conducted with the exception that the charge-transporting material was changed to prepare photoreceptors, and measurements were then made for the same items. The used charge-transporting materials and the measured results are set forth in Table 2.

EXAMPLE 13

The same procedure as in Example 1 was conducted with the exception that a disazo dye (CG-3) represented by the structural formula

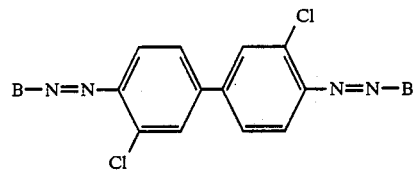

wherein B is a group having the formula

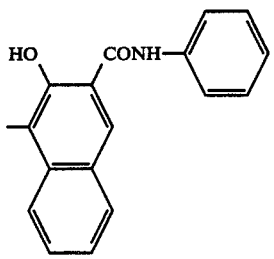

was employed as a charge-generating material to prepare a photoreceptor, and measurements were then made for the same items.

EXAMPLE 14

The same procedure as in Example 1 was conducted with the exception that τ-phthalocyanine (CG-4) was used as a charge-generating material, to prepare a photoreceptor, and measurements were then made for the same items.

EXAMPLES 15 to 90

Following the manner of Example 1 with the exception that other charge-generating materials and charge-transporting materials were used, photoreceptors were prepared, and measurements were then made. As charge-generating materials, there were used azo compounds represented by the general formulae (II), (III) and (IV). Combinations of the used charge-generating materials and charge-transporting materials are set forth in Table 2. In this table, the used charge-generating materials are shown by symbols of the general formulae and the above-mentioned couplers.

COMPARATIVE EXAMPLE 1

The same procedure as in Example 1 was conducted with the exception that disazo dye (CG-3) represented by the structural formula

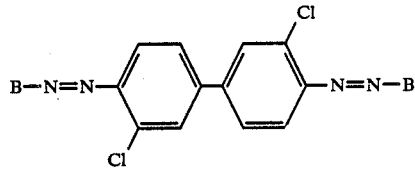

wherein B is a group having the formula

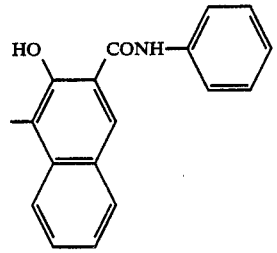

was used as a charge-generating material and 2,5-bis(4-diethylaminophenyl)-1,3,4-oxadiazole (CT-1) was used as a charge-transporting material, to prepare a photoreceptor, and the operation of electrification exposure was repeated 1,000 times.

The measured results of Examples 1 to 90 and Comparative Example 1 are set forth in Table 2.

TABLE 2

| Example | Charge-Generating Material | Charge-Transporting Material | Number of Repeated Operation | $V_0$ (V) | $V_2$ (V) | $V_{12}$ (V) | $E_{\frac{1}{2}}$ (lux · sec) |
|---|---|---|---|---|---|---|---|
| Example 1 | CG-1 | Compound No. 8 | 1 | −1120 | −1080 | 0 | 1.2 |
|  |  |  | 1000 | −1060 | −1010 | 0 | 1.3 |
| Example 2 | " | Compound No. 7 | 1 | −1004 | −980 | 0 | 2.0 |
|  |  |  | 1000 | −990 | −970 | −1 | 2.0 |
| Example 3 | " | Compound No. 3 | 1 | −1210 | −1130 | −1 | 2.2 |
|  |  |  | 1000 | −1220 | −1120 | −2 | 2.6 |
| Example 4 | " | Compound No. 14 | 1 | −990 | −940 | −1 | 2.0 |
|  |  |  | 1000 | −940 | −900 | −1 | 2.8 |
| Example 5 | " | Compound No. 21 | 1 | −1310 | −1270 | 0 | 3.6 |
|  |  |  | 1000 | −1290 | −1200 | 0 | 4.2 |
| Example 6 | " | Compound No. 27 | 1 | −1230 | −1150 | −1 | 2.8 |
|  |  |  | 1000 | −1220 | −1130 | −1 | 3.1 |
| Example 7 | CG-2 | Compound No. 8 | 1 | −980 | −965 | 0 | 2.0 |
|  |  |  | 1000 | −970 | −950 | 0 | 2.4 |
| Example 8 | " | Compound No. 7 | 1 | −980 | −950 | 0 | 2.3 |
|  |  |  | 1000 | −970 | −945 | 0 | 2.4 |
| Example 9 | " | Compound No. 3 | 1 | −995 | −960 | −2 | 2.4 |
|  |  |  | 1000 | −940 | −925 | −2 | 3.1 |
| Example 10 | " | Compound No. 14 | 1 | −1130 | −1065 | 0 | 2.1 |
|  |  |  | 1000 | −1085 | −1000 | 0 | 2.2 |
| Example 11 | " | Compound No. 21 | 1 | −1015 | −980 | −1 | 1.8 |
|  |  |  | 1000 | −975 | −940 | −2 | 1.9 |
| Example 12 | " | Compound No. 27 | 1 | −1130 | −1065 | 0 | 3.2 |
|  |  |  | 1000 | −1080 | −1010 | −2 | 4.9 |
| Example 13 | CG-3 | Compound No. 8 | 1 | −815 | −795 | −1 | 1.8 |
|  |  |  | 1000 | −810 | −770 | −2 | 2.1 |
| Example 14 | CG-4 | Compound No. 8 | 1 | −855 | −820 | −3 | 2.3 |
|  |  |  | 1000 | −840 | −800 | −3 | 2.6 |
| Example 15 | (II)-(A-1) | Compound No. 7 | 1 | −1105 | −950 | 0 | 2.5 |
|  |  |  | 1000 | −1110 | −940 | −1 | 2.5 |
| Example 16 | (II)-(A-1) | Compound No. 8 | 1 | −1170 | −1100 | −1 | 2.1 |
|  |  |  | 1000 | −1115 | −1060 | −1 | 2.5 |
| Example 17 | (II)- | Compound | 1 | −1150 | −1090 | 0 | 2.4 |

TABLE 2-continued

| Example | Charge-Generating Material | Charge-Transporting Material | Number of Repeated Operation | $V_0$ (V) | $V_2$ (V) | $V_{12}$ (V) | $E_{\frac{1}{2}}$ (lux·sec) |
|---|---|---|---|---|---|---|---|
| | (A-1) | No. 24 | 1000 | −1100 | −1060 | 0 | 3.1 |
| Example 18 | (II)-(A-1) | Compound No. 30 | 1<br>1000 | −1220<br>−1150 | −1170<br>−1100 | −2<br>−5 | 3.4<br>3.9 |
| Example 19 | (II)-(A-9) | Compound No. 7 | 1<br>1000 | −990<br>−980 | −940<br>−935 | −1<br>−1 | 2.2<br>2.2 |
| Example 20 | (II)-(A-9) | Compound No. 8 | 1<br>1000 | −1150<br>−1110 | −1070<br>−1020 | 0<br>−1 | 2.3<br>3.8 |
| Example 21 | (II)-(A-9) | Compound No. 24 | 1<br>1000 | −1170<br>−1100 | −1110<br>−1050 | −1<br>−3 | 2.8<br>3.6 |
| Example 22 | (II)-(A-9) | Compound No. 30 | 1<br>1000 | −1150<br>−1095 | −1070<br>−1030 | −2<br>−3 | 3.6<br>4.4 |
| Example 23 | (II)-(A-21) | Compound No. 7 | 1<br>1000 | −1010<br>−1000 | −980<br>−980 | −1<br>−1 | 2.5<br>2.7 |
| Example 24 | (II)-(A-21) | Compound No. 8 | 1<br>1000 | −1190<br>−1120 | −1120<br>−1050 | 0<br>0 | 2.0<br>2.6 |
| Example 25 | (II)-(A-21) | Compound No. 24 | 1<br>1000 | −1220<br>−1140 | −1150<br>−1060 | 0<br>−2 | 3.6<br>4.4 |
| Example 26 | (II)-(A-21) | Compound No. 30 | 1<br>1000 | −1270<br>−1180 | −1200<br>−1100 | −1<br>−3 | 3.2<br>3.9 |
| Example 27 | (II)-(A-49) | Compound No. 7 | 1<br>1000 | −1140<br>−1150 | −1010<br>−1000 | 0<br>−1 | 2.1<br>2.2 |
| Example 28 | (II)-(A-49) | Compound No. 8 | 1<br>1000 | −1210<br>−1160 | −1140<br>−1110 | 0<br>−1 | 2.2<br>2.6 |
| Example 29 | (II)-(A-49) | Compound No. 24 | 1<br>1000 | −1220<br>−1170 | −1145<br>−1090 | −3<br>−5 | 3.1<br>3.8 |
| Example 30 | (II)-(A-49) | Compound No. 30 | 1<br>1000 | −1070<br>−1020 | −1015<br>−960 | −1<br>−2 | 2.4<br>3.5 |
| Example 31 | (II)-(A-120) | Compound No. 7 | 1<br>1000 | −980<br>−985 | −970<br>−975 | 0<br>0 | 2.5<br>2.5 |
| Example 32 | (II)-(A-120) | Compound No. 8 | 1<br>1000 | −1110<br>−1080 | −1050<br>−1040 | −1<br>−2 | 2.2<br>2.6 |
| Example 33 | (II)-(A-120) | Compound No. 24 | 1<br>1000 | −1220<br>−1120 | −1140<br>−1040 | −3<br>−5 | 3.4<br>4.2 |
| Example 34 | (II)-(A-120) | Compound No. 30 | 1<br>1000 | −1230<br>−1150 | −1110<br>−1050 | 0<br>−1 | 2.6<br>3.6 |
| Example 35 | (III)-(A-1) | Compound No. 7 | 1<br>1000 | −1220<br>−1240 | −1150<br>−1170 | 0<br>0 | 2.0<br>2.0 |
| Example 36 | (III)-(A-1) | Compound No. 8 | 1<br>1000 | −1110<br>−1070 | −1060<br>−1010 | −2<br>−3 | 2.4<br>2.9 |
| Example 37 | (III)-(A-1) | Compound No. 24 | 1<br>1000 | −1040<br>−1010 | −1000<br>−960 | 0<br>−2 | 2.9<br>3.5 |
| Example 38 | (III)-(A-1) | Compound No. 30 | 1<br>1000 | −1210<br>−1140 | −1150<br>−1080 | −1<br>−2 | 2.8<br>3.1 |
| Example 39 | (III)-(A-9) | Compound No. 7 | 1<br>1000 | −1000<br>−970 | −920<br>−910 | 0<br>−1 | 2.1<br>2.2 |
| Example 40 | (III)-(A-9) | Compound No. 8 | 1<br>1000 | −1250<br>−1200 | −1185<br>−1140 | 0<br>−1 | 2.5<br>2.9 |
| Example 41 | (III)-(A-9) | Compound No. 24 | 1<br>1000 | −1040<br>−970 | −990<br>−910 | 0<br>0 | 3.2<br>4.2 |
| Example 42 | (III)-(A-9) | Compound No. 30 | 1<br>1000 | −1160<br>−1090 | −1110<br>−1020 | −3<br>−5 | 3.4<br>4.5 |
| Example 43 | (III)-(A-21) | Compound No. 7 | 1<br>1000 | −1230<br>−1200 | −1150<br>−1110 | 0<br>−1 | 2.0<br>2.0 |
| Example 44 | (III)-(A-21) | Compound No. 8 | 1<br>1000 | −1220<br>−1130 | −1150<br>−1090 | 0<br>−1 | 2.2<br>2.4 |
| Example 45 | (III)-(A-21) | Compound No. 24 | 1<br>1000 | −1210<br>−1180 | −1160<br>−1120 | −1<br>−2 | 3.0<br>3.8 |
| Example 46 | (III)-(A-21) | Compound No. 30 | 1<br>1000 | −970<br>−940 | −920<br>−890 | −3<br>−5 | 2.6<br>3.5 |
| Example 47 | (III)-(A-49) | Compound No. 7 | 1<br>1000 | −1030<br>−990 | −980<br>−910 | −1<br>−1 | 2.1<br>2.2 |
| Example 48 | (III)-(A-49) | Compound No. 8 | 1<br>1000 | −1180<br>−1150 | −1120<br>−1080 | 0<br>0 | 2.0<br>2.6 |
| Example 49 | (III)-(A-49) | Compound No. 24 | 1<br>1000 | −1120<br>−1080 | −1085<br>−1020 | −3<br>−5 | 3.6<br>4.4 |
| Example 50 | (III)-(A-49) | Compound No. 30 | 1<br>1000 | −1240<br>−1190 | −1155<br>−1080 | 0<br>−2 | 2.2<br>3.2 |
| Example 51 | (III)-(A-134) | Compound No. 7 | 1<br>1000 | −1040<br>−1030 | −940<br>−940 | 0<br>0 | 1.9<br>2.0 |
| Example 52 | (III)-(A-134) | Compound No. 8 | 1<br>1000 | −1140<br>−1100 | −1070<br>−1050 | −1<br>−1 | 2.2<br>2.8 |
| Example 53 | (III)-(A-134) | Compound No. 24 | 1<br>1000 | −1180<br>−1110 | −1120<br>−1040 | −2<br>−5 | 3.8<br>4.3 |
| Example 54 | (III)-(A-134) | Compound No. 30 | 1<br>1000 | −1210<br>−1150 | −1130<br>−1020 | 0<br>−1 | 2.9<br>3.6 |
| Example 55 | (IV)-(A-1) | Compound No. 7 | 1<br>1000 | −995<br>−1010 | −960<br>−970 | 0<br>0 | 1.8<br>1.9 |
| Example 56 | (IV)- | Compound | 1 | −1065 | −990 | 0 | 2.1 |

TABLE 2-continued

| Example | Charge-Generating Material | Charge-Transporting Material | Number of Repeated Operation | $V_0$ (V) | $V_2$ (V) | $V_{12}$ (V) | $E_{\frac{1}{2}}$ (lux · sec) |
|---|---|---|---|---|---|---|---|
| | (A-1) | No. 8 | 1000 | −1020 | −960 | 0 | 2.9 |
| Example 57 | (IV)-(A-1) | Compound No. 24 | 1 | −1210 | −1130 | −1 | 2.8 |
| | | | 1000 | −1220 | −1120 | −2 | 3.6 |
| Example 58 | (IV)-(A-1) | Compound No. 30 | 1 | −1190 | −1120 | −2 | 3.0 |
| | | | 1000 | −1120 | −1070 | −5 | 3.8 |
| Example 59 | (IV)-(A-9) | Compound No. 7 | 1 | −1020 | −975 | −1 | 1.9 |
| | | | 1000 | −1000 | −970 | −1 | 1.9 |
| Example 60 | (IV)-(A-9) | Compound No. 8 | 1 | −1230 | −1150 | −1 | 2.8 |
| | | | 1000 | −1220 | −1130 | −1 | 3.1 |
| Example 61 | (IV)-(A-9) | Compound No. 24 | 1 | −1180 | −1165 | 0 | 2.0 |
| | | | 1000 | −1170 | −1150 | 0 | 2.4 |
| Example 62 | (IV)-(A-9) | Compound No. 30 | 1 | −1090 | −1065 | −1 | 3.6 |
| | | | 1000 | −1060 | −1030 | −3 | 4.8 |
| Example 63 | (IV)-(A-21) | Compound No. 7 | 1 | −980 | −965 | 0 | 2.4 |
| | | | 1000 | −970 | −950 | −1 | 2.6 |
| Example 64 | (IV)-(A-21) | Compound No. 8 | 1 | −1100 | −1040 | 0 | 2.0 |
| | | | 1000 | −1050 | −980 | −1 | 2.4 |
| Example 65 | (IV)-(A-21) | Compound No. 24 | 1 | −1220 | −1150 | −2 | 2.8 |
| | | | 1000 | −1180 | −1120 | −5 | 3.9 |
| Example 66 | (IV)-(A-21) | Compound No. 30 | 1 | −1090 | −1020 | −3 | 3.2 |
| | | | 1000 | −1010 | −920 | −5 | 4.2 |
| Example 67 | (IV)-(A-49) | Compound No. 7 | 1 | −1170 | −1140 | −1 | 1.7 |
| | | | 1000 | −1080 | −1030 | −1 | 1.8 |
| Example 68 | (IV)-(A-49) | Compound No. 8 | 1 | −1210 | −1150 | 0 | 2.2 |
| | | | 1000 | −1190 | −1130 | −1 | 2.6 |
| Example 69 | (IV)-(A-49) | Compound No. 24 | 1 | −1200 | −1165 | 0 | 2.9 |
| | | | 1000 | −1170 | −1125 | 0 | 3.3 |
| Example 70 | (IV)-(A-49) | Compound No. 30 | 1 | −990 | −955 | −1 | 3.6 |
| | | | 1000 | −950 | −930 | −3 | 4.8 |
| Example 71 | (IV)-(A-53) | Compound No. 7 | 1 | −1170 | −1050 | 0 | 1.4 |
| | | | 1000 | −1200 | −1040 | 0 | 1.4 |
| Example 72 | (IV)-(A-53) | Compound No. 8 | 1 | −1150 | −1100 | 0 | 1.8 |
| | | | 1000 | −1095 | −1050 | 0 | 2.2 |
| Example 73 | (IV)-(A-53) | Compound No. 24 | 1 | −980 | −950 | −2 | 2.8 |
| | | | 1000 | −900 | −880 | −3 | 3.2 |
| Example 74 | (IV)-(A-53) | Compound No. 30 | 1 | −1020 | −990 | 0 | 2.0 |
| | | | 1000 | −940 | −890 | −2 | 3.2 |
| Example 75 | (IV)-(A-66) | Compound No. 7 | 1 | −1040 | −970 | −1 | 1.0 |
| | | | 1000 | −1050 | −970 | −1 | 1.0 |
| Example 76 | (IV)-(A-66) | Compound No. 8 | 1 | −1180 | −1110 | −3 | 3.8 |
| | | | 1000 | −1120 | −1070 | −5 | 4.2 |
| Example 77 | (IV)-(A-66) | Compound No. 24 | 1 | −1240 | −1180 | 0 | 2.7 |
| | | | 1000 | −1170 | −1085 | −2 | 3.5 |
| Example 78 | (IV)-(A-66) | Compound No. 30 | 1 | −1040 | −980 | −1 | 3.7 |
| | | | 1000 | −975 | −920 | −1 | 4.2 |
| Example 79 | (IV)-(A-122) | Compound No. 7 | 1 | −1100 | −1020 | −1 | 2.1 |
| | | | 1000 | −1050 | −1000 | −1 | 2.1 |
| Example 80 | (IV)-(A-122) | Compound No. 8 | 1 | −1210 | −1160 | −1 | 2.6 |
| | | | 1000 | −1145 | −1080 | −2 | 2.9 |
| Example 81 | (IV)-(A-122) | Compound No. 24 | 1 | −1120 | −1080 | 0 | 3.3 |
| | | | 1000 | −1070 | −1010 | −3 | 3.7 |
| Example 82 | (IV)-(A-122) | Compound No. 30 | 1 | −1020 | −970 | −1 | 2.5 |
| | | | 1000 | −950 | −910 | −1 | 3.4 |
| Example 83 | (IV)-(A-153) | Compound No. 7 | 1 | −890 | −800 | −1 | 0.8 |
| | | | 1000 | −900 | −800 | −1 | 0.8 |
| Example 84 | (IV)-(A-153) | Compound No. 8 | 1 | −1120 | −1010 | 0 | 0.9 |
| | | | 1000 | −1100 | −1000 | 0 | 0.9 |
| Example 85 | (IV)-(A-154) | Compound No. 7 | 1 | −1220 | −1170 | 0 | 1.1 |
| | | | 1000 | −1190 | −1090 | −1 | 1.2 |
| Example 86 | (IV)-(A-154) | Compound No. 8 | 1 | −1030 | −960 | −1 | 1.1 |
| | | | 1000 | −1050 | −970 | −1 | 1.1 |
| Example 87 | (IV)-(A-155) | Compound No. 7 | 1 | −1110 | −1010 | 0 | 1.2 |
| | | | 1000 | −1100 | −1000 | −1 | 1.2 |
| Example 88 | (IV)-(A-155) | Compound No. 8 | 1 | −990 | −900 | −1 | 1.1 |
| | | | 1000 | −980 | −870 | −1 | 1.1 |
| Example 89 | (IV)-(A-59) | Compound No. 7 | 1 | −1170 | −1050 | 0 | 1.5 |
| | | | 1000 | −1150 | −1010 | −1 | 1.6 |
| Example 90 | (IV)-(A-59) | Compound No. 8 | 1 | −940 | −890 | 0 | 1.3 |
| | | | 1000 | −950 | −890 | 0 | 1.4 |
| Comp. Ex. 1 | CG-3 | CT-1 | 1 | −1040 | −950 | −5 | 5.6 |
| | | | 1000 | −975 | −890 | −17 | 16.2 |

EXAMPLES 91 TO 99

The photoreceptors of the present invention prepared in Examples 1, 15, 16, 35, 36, 55, 56, 83 and 84 were used in a commercially available electrophotographic copier, and copying operation was then made. In consequence, it was found that these photoreceptors could provide fog-free clear images which were faithful to an original even on the ten thousandth sheet of the copies.

What is claimed is:

1. An electrophotographic photoreceptor comprising an electrically conductive base and a photosensitive layer thereon containing a charge-generating material and a charge-transporting material wherein said charge-transporting material comprises a tetraphenylthiophene of the formula

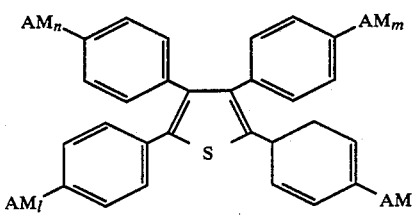

wherein AM is a tertiary amino group and each of l, m and n is the integer 0 or 1 and $1 \geq m \geq n$.

2. An electrophotographic photoreceptor as claimed in claim 1, wherein the tetraphenylthiophene AM is of the formula $-NR_1R_2$ in which each of $R_1$ and $R_2$ is a phenyl group
 or a naphthyl group which is unsubstituted or substituted by at least one of a halogen atom, alkyl of 1 to 8 carbon atoms, alkoxy of 1 to 5 carbon atoms, a carboxylate group of 1 to 6 carbon atoms, an aralkyl group of 7 to 10 carbon atoms, a phenyl group and a naphthyl group.

3. An electrophotographic photoreceptor as claimed in claim 2, wherein each of $R_1$ and $R_2$ is phenyl, benzyl, naphthyl or phenyl substituted by halogen, lower alkyl, lower alkoxy, or carbo-lower alkoxy.

4. A photoreceptor as claimed in claim 1, wherein each of l, m and n are 0.

5. A photoreceptor as claimed in claim 1, where l is 1 and m and n or 0.

6. A photoreceptor as claimed in claim 1, wherein l and m are 1, and n is 0.

7. A photorecptor as claimed in claim 1, wherein l, m and n are 1.

8. An electrophotographic photoreceptor as claimed in claim 1 wherein the photosensitive layer comprises two layers, one of which contains a charge-generating material and the other of which contains a charge-transporting material.

9. An electrophotographic photoreceptor as claimed in claim 1 wherein the thickness of the charge-generating layer is 0.05 to 2 μm and the thickness of the charge-transporting-transporting layer is 5 to 30 μm.

10. An electrophotographic photoreceptor as claimed in claim 1 wherein the charge-generating material is an azo compound or phthalocyanine.

11. An electrophotographic photoreceptor as claimed in claim 1 wherein said charge-generating material is an azo compound represented by the general formula (II), (III) or (IV)

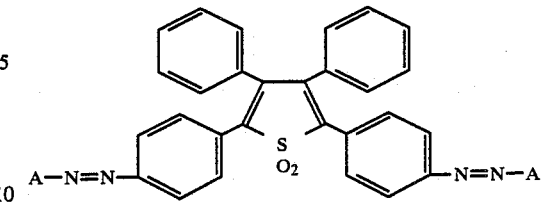

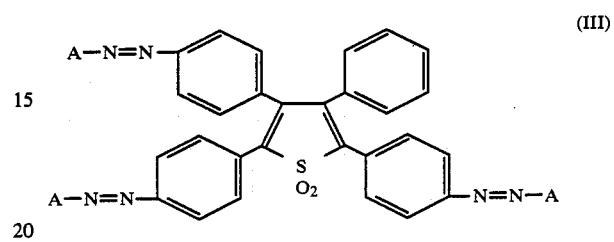

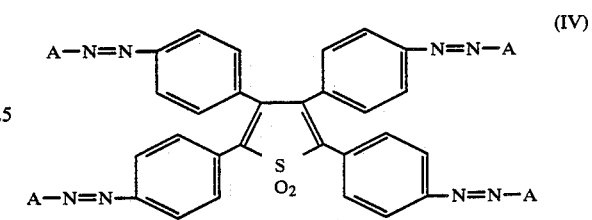

wherein A in formulae (II), (III) and (IV) is a coupler residuum.

12. An electrophotographic photoreceptor as claimed in claim 1 wherein the charge-generating material is a compound of the formula

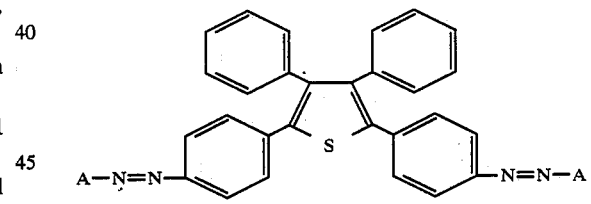

wherein A is a group having the formula

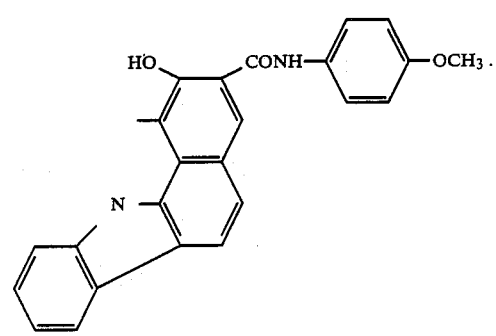

13. An electrophotographic photoreceptor as claimed in claim 1 wherein the charge-generating material is a compound of the formula

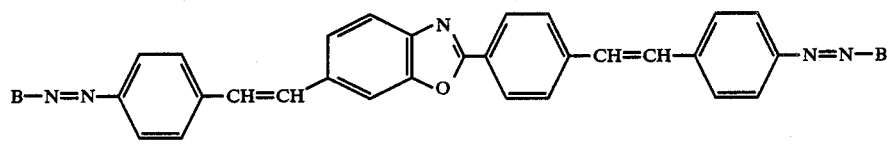
wherein B is a group having the formula
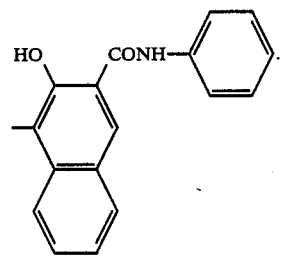
* * * * *